(12) United States Patent
Chakravarty et al.

(10) Patent No.: US 7,790,640 B2
(45) Date of Patent: Sep. 7, 2010

(54) ABSORBENT ARTICLES HAVING BIODEGRADABLE NONWOVEN WEBS

(75) Inventors: Jayant Chakravarty, Appleton, WI (US); Vasily A. Topolkaraev, Appleton, WI (US); Cliff J. Ellis, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 109 days.

(21) Appl. No.: 11/387,314

(22) Filed: Mar. 23, 2006

(65) Prior Publication Data

US 2007/0224903 A1 Sep. 27, 2007

(51) Int. Cl.
*D04H 1/00* (2006.01)
*A61F 13/15* (2006.01)

(52) U.S. Cl. .................. 442/335; 442/334; 442/338; 442/327; 442/361; 442/364; 604/358

(58) Field of Classification Search ................. 442/335, 442/338, 361, 327, 334, 364; 604/358
See application file for complete search history.

(56) References Cited

U.S. PATENT DOCUMENTS

| 4,340,563 | A | 7/1982 | Appel et al. |
|---|---|---|---|
| 4,526,733 | A | 7/1985 | Lau |
| 4,719,246 | A | 1/1988 | Murdoch et al. |
| 4,766,182 | A | 8/1988 | Murdoch et al. |
| 4,800,219 | A | 1/1989 | Murdoch et al. |
| 4,902,515 | A | 2/1990 | Loomis et al. |
| 4,981,696 | A | 1/1991 | Loomis et al. |
| 5,069,970 | A | 12/1991 | Largman et al. |
| 5,160,746 | A | 11/1992 | Dodge et al. |
| 5,271,883 | A | 12/1993 | Timmons et al. |
| 5,317,064 | A | 5/1994 | Spinu |
| 5,336,552 | A | 8/1994 | Strack et al. |
| 5,366,793 | A | 11/1994 | Fitts et al. |
| 5,382,400 | A | 1/1995 | Pike et al. |
| 5,486,166 | A | 1/1996 | Bishop et al. |
| 5,490,846 | A | 2/1996 | Ellis et al. |
| 5,562,650 | A | 10/1996 | Everett et al. |
| 5,652,048 | A | 7/1997 | Haynes et al. |
| 5,698,322 | A | 12/1997 | Tsai et al. |

(Continued)

FOREIGN PATENT DOCUMENTS

| EP | 1504739 | A | 2/2005 |
|---|---|---|---|
| WO | 0019957 | A | 4/2000 |
| WO | 0044411 | A1 | 8/2000 |
| WO | 0134886 | A | 5/2001 |
| WO | 0148291 | A | 7/2001 |
| WO | 0149912 | A | 7/2001 |
| WO | 02098659 | A | 12/2002 |

OTHER PUBLICATIONS

International Search Report and Written Opinion for PCT/IB2007/050797 dated Aug. 16, 2007.

(Continued)

*Primary Examiner*—Rena L Dye
*Assistant Examiner*—Jennifer Steele
(74) *Attorney, Agent, or Firm*—Armstrong Teasdale LLP

(57) ABSTRACT

The present disclosure generally relates to absorbent articles. More specifically, the present disclosure relates to an absorbent article comprising a surge management layer comprising a nonwoven web. The nonwoven web includes a filler fiber and a binder fiber. A portion of the cross-sectional area of the filler fiber is hollow, and the binder fiber includes a sheath component and a core component.

19 Claims, 2 Drawing Sheets

U.S. PATENT DOCUMENTS

| | | | |
|---|---|---|---|
| 5,759,926 | A | 6/1998 | Pike et al. |
| 5,820,973 | A | 10/1998 | Dodge et al. |
| 5,879,343 | A | 3/1999 | Dodge et al. |
| 5,989,688 | A * | 11/1999 | Barge et al. .................. 428/198 |
| 5,994,615 | A | 11/1999 | Dodge et al. |
| 6,368,990 | B1 | 4/2002 | Jennergen et al. |
| 6,506,873 | B1 * | 1/2003 | Ryan et al. .................. 528/354 |
| 6,582,639 | B2 | 6/2003 | Nellis |
| 6,649,547 | B1 | 11/2003 | Arnold et al. |
| 6,881,876 | B2 | 4/2005 | Nurmi et al. |
| 6,953,622 | B2 | 10/2005 | Tsai et al. |
| 2003/0022581 | A1 * | 1/2003 | Tsai et al. .................. 442/364 |
| 2003/0148688 | A1 * | 8/2003 | Matsunaga et al. .......... 442/327 |
| 2004/0170836 | A1 * | 9/2004 | Bond et al. .................. 428/398 |
| 2004/0265579 | A1 * | 12/2004 | Dugan ........................ 428/364 |

OTHER PUBLICATIONS

Dugan, Jeffrey S., "Novel Properties of PLA Fibers", TAPPI Nonwovens Conference proceedings, 2000.

Huang, J. et al., Crystallization and Microstructure of Poly(L-lactide-co-meso-lactide) Copolymers; Macromolecules; 1998; 31(8); 2593-2599.

Baratian, S. et al., Crystallization and Solid-State Structure of Random Polylactide Copolymers: Poly(L-lactide-co-D-lactide)s; Macromolecules; 2001; 34(14); 4857-4864.

* cited by examiner

ABSORBENT ARTICLES HAVING BIODEGRADABLE NONWOVEN WEBS

FIELD OF THE DISCLOSURE

The present disclosure generally relates to absorbent articles. More specifically, the present disclosure relates to an absorbent article including a surge management layer including a nonwoven web. The nonwoven web includes a filler fiber and a binder fiber. A portion of the cross-sectional area of the filler fiber is hollow, and the binder fiber includes a sheath component and a core component. A number of biodegradable materials can be used to construct the nonwoven web.

BACKGROUND OF THE DISCLOSURE

Among the various desired performance objectives for personal care absorbent products is low leakage from the product after insult and a dry feel to the wearer or user. Absorbent articles commonly fail before the total absorbent capacity of the product has been utilized. Absorbent garments, such as incontinence garments and disposable diapers, often leak at the legs and the waist. The leakage can be the result of a variety of shortcomings in the product; one particular one being insufficient fluid uptake by the absorbent system, particularly during high liquid volume insults or on the third liquid insult.

It has been found that urination can occur at rates as high as 15 to 20 milliliters per second and velocities as high as 280 centimeters per second. Conventional absorbent articles may initially uptake fluid at a rate of only 8 milliliters per second or less. In addition, the initial uptake rates for conventional absorbent structures can deteriorate after receiving prior liquid surges into their structures. The disparity between liquid delivery and uptake rates can result in excessive pooling on the surface of the absorbent fabric before the liquid is taken-up by the absorbent core. During this time, pooled liquid can leak from the leg openings of the diaper and soil the outer clothing and/or the bedding of the wearer. Attempts to alleviate this leakage have included providing physical barriers with such design features as elastic leg gathers, as well as changing the amount and/or configuration of the absorbent material in the zone of the structure into which the liquid surges typically occur. Absorbent gelling particles such as superabsorbent polymers have also been included to increase the liquid holding capacity in various regions of the absorbent structure; such absorbent gelling particles, however, may not have the rapid uptake rates of conventional materials such as wood pulp and fluff which are also commonly used in absorbent cores. As a result, as the amount of absorbent gelling particles in the absorbent core structures are increased in modern day diapers, oftentimes the initial uptake rate will tend to decrease.

One important component of many personal care products is the fluid surge management layer, which is typically placed under the liner and above a superabsorbent layer. The surge management layer (also referred to as the surge layer, surge material, intake layer, transfer layer, transport layer, and the like) manages the flow of fluids to the superabsorbent layer. Fluid management is generally measured by the properties of void volume and permeability. If the surge material permeability is too high, the fluid will permeate the superabsorbent material too quickly, causing it to be overwhelmed. If permeability is too low, the fluid will not progress to the superabsorbent material and can "back-up" and pool into and on the liner. The surge management layer should also have a sufficient void volume to provide temporary storage for incoming liquid.

Conventional surge materials include biodegradable and non-biodegradable fibers to achieve the desired processability and physical properties, such as void volume, compressability, resiliency, and permeability. Conventional methods of producing such surge materials have included bonded carded web processes, which produce a nonwoven web.

The bonded carded web process generally requires the use of staple cut fibers, typically in a length of approximately 1 to 3 inches. In order to give the nonwoven web integrity after processing, at least one of the fiber components includes a thermoplastic material that is at least partially melted or softened to bind the web together to make a cohesive layer. Such a component is commonly referred to as a binder fiber.

One shortcoming of the bonded carded web process involves the collapse of the web during or after bonding at elevated temperatures, resulting in a nonwoven web having inferior intake properties. Web collapse can occur during bonding due to the relatively high temperatures used to soften and partially melt at least one of the fiber components. Web collapse can also occur due to the mechanical force required to either pass hot air through the web structure or compress the web structure against one or more rolls or conveyors. Additionally, web collapse can occur when the web is wound into a roll after bonding. The hot fibers may still be soft and pliable (e.g., above the glass transition temperature for the particular fibers), and the internal pressures of the roll can cause the web to collapse. As the web cools inside the roll, the fibers will slowly conform to their existing spatial alignment until the temperature reaches or falls below the glass transition temperature.

As such, a need in the industry exists for a nonwoven web for use in a surge management layer in an absorbent article, the nonwoven web having a bulky, resilient structure and possessing the various desired properties described above.

SUMMARY OF THE DISCLOSURE

The present disclosure relates to an absorbent article including a surge management layer including a nonwoven web. The nonwoven web includes a filler fiber and a binder fiber. A portion of the cross-sectional area of the filler fiber is hollow. The binder fiber includes a sheath component and a core component. In various embodiments, the filler fiber, the sheath component, and/or the core component each include a biodegradable polylactic acid polymer.

Briefly, therefore, the present disclosure is directed to an absorbent article comprising a surge management layer comprising a nonwoven web. The nonwoven web comprises from about 10% (by weight nonwoven web) to about 80% (by weight nonwoven web) of a filler fiber. The nonwoven web also includes from about 20% (by weight nonwoven web) to about 90% (by weight nonwoven web) of a binder fiber including a sheath component and a core component. The filler fiber is from about 5% (by cross-sectional area) to about 50% (by cross-sectional area) hollow, and the binder fiber comprises from about 10% (by cross-sectional area) to about 70% (by cross-sectional area) sheath component.

Other objects and features will be in part apparent and in part pointed out hereinafter.

ABBREVIATIONS AND DEFINITIONS

Figure 1A:
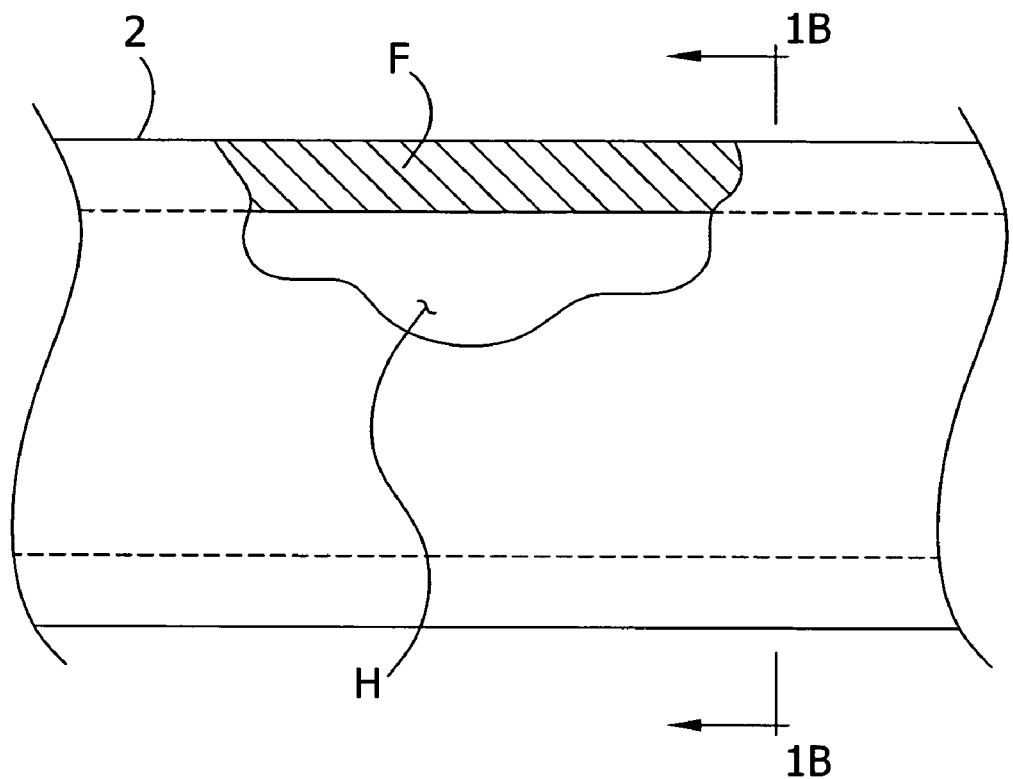
FIGS. 1A and 1B are longitudinal (FIG. 1A) and cross-sectional (FIG. 1B) views of the filler fiber of the present disclosure.

The following definitions and methods are provided to better define the present disclosure and to guide those of ordinary skill in the art in the practice of the present disclosure. Unless otherwise noted, terms are to be understood according to conventional usage by those of ordinary skill in the relevant art.

As used herein the term "nonwoven" fabric or web means a web having a structure of individual fibers or threads which are interlaid, but not in an identifiable manner as in a knitted or woven fabric. Nonwoven fabrics or webs can be formed by various processes including, but not limited to, meltblowing processes and spunbonding processes.

As used herein the term "spunbond fibers" refers to small diameter fibers of mechanically and/or eductively drawn polymeric material. Spunbond fibers are generally formed by extruding molten thermoplastic material as filaments from a plurality of fine capillaries of a spinneret with the diameter of the extruded filaments then being rapidly reduced. Examples of spunbond fibers and methods of making the same are described in, by way of example only, U.S. Pat. No. 4,340,563 to Appel et al., U.S. Pat. No. 5,382,400 to Pike et al., and U.S. Pat. No. 5,795,926 to Pike et al.; the entire content of the aforesaid patents are hereby incorporated by reference herein. Spunbond fibers are generally not tacky when they are deposited onto a collecting surface and are continuous.

As used herein the term "meltblown fibers" means fibers of polymeric material which are generally formed by extruding a molten thermoplastic material through a plurality of die capillaries as molten threads or filaments into converging high velocity air streams which attenuate the filaments of molten thermoplastic material to reduce their diameter. Thereafter, the meltblown fibers can be carried by the high velocity gas stream and are deposited on a collecting surface to form a web of randomly dispersed meltblown fibers. Meltblowing processes are disclosed in, by way of example only, in U.S. Pat. No. 5,271,883 to Timmons et al.; U.S. Pat. No. 5,160,746 to Dodge et al.; U.S. Pat. No. 4,526,733 to Lau; U.S. Pat. No. 5,652,048 to Haynes et al.; and U.S. Pat. No. 5,366,793 to Fitts et al.; the entire contents of the aforesaid patents are hereby incorporated by reference herein. Meltblown fibers are generally smaller than about 10 micrometers in average diameter and, unlike spunbond fibers, are generally tacky when deposited onto a collecting surface, thereby bonding to one another during the deposition step.

As used herein the term "biodegradable" is meant to represent that a material degrades from the action of naturally occurring microorganisms such as bacteria, fungi, and algae. The biodegradability of a material may be determined using ASTM Test Method 5338.92 or ISO CD Test Method 14855.

DETAILED DESCRIPTION OF THE DISCLOSURE

The present disclosure is generally directed to fluid management materials in personal care articles. Specifically, the present disclosure relates to an absorbent article including a surge management layer including a nonwoven web. The nonwoven webs of the present disclosure include a filler fiber and a binder fiber. A portion of the filler fiber is hollow, and the binder fiber includes a sheath component and a core component. In various embodiments, the filler fiber, the sheath component, and/or the core component each include a polylactic acid polymer. It has been found that a high quality, low cost nonwoven web for use in constructing the surge management layer of an absorbent article may be produced using the various components and amounts thereof described herein.

The nonwoven webs of the present disclosure, which can be used as surge management layers in absorbent articles as noted herein, possess various desirable characteristics such as, for example, bulkiness and resiliency. The bulky and resilient nonwoven webs comprising the surge management layer can remain substantially open under load, generally maintaining void volume in the web. Moreover, the nonwoven webs substantially resist collapse during processing and/or when wetted, which results in the relatively effective release of liquid and relatively effective desorption of the web. Additionally, the nonwoven webs possess the desired compressibility to be regenerated after being wetted to preserve void volume capacity for successive insults, and are constructed from biodegradable materials.

I. The Filler Fiber

As noted above, the nonwoven web includes a filler fiber. The filler fiber generally provides strength and/or rigidity to the nonwoven web. The filler fiber may bind with portions of the binder fiber (described in detail below) to form the structure of the nonwoven web.

The nonwoven web comprises from about 10% (by weight nonwoven web) to about 80% (by weight nonwoven web) filler fiber. For example, the nonwoven web may comprise greater than about 25% (by weight nonwoven web) filler fiber; greater than about 35% (by weight nonwoven web) filler fiber; greater than about 65% (by weight nonwoven web) filler fiber; or greater than about 75% (by weight nonwoven web) filler fiber. In some embodiments, the nonwoven web comprises from about 30% (by weight nonwoven web) to about 70% (by weight nonwoven web) filler fiber. For example, the nonwoven web may comprise greater than about 40% (by weight nonwoven web) filler fiber; greater than about 50% (by weight nonwoven web) filler fiber; or greater than about 60% (by weight nonwoven web) filler fiber. Alternatively, the nonwoven web comprises from about 40% (by weight nonwoven web) to about 60% (by weight nonwoven web) filler fiber. For example, the nonwoven web may comprise greater than about 45% (by weight nonwoven web) filler fiber; or greater than about 55% (by weight nonwoven web) filler fiber.

The filler fiber is formed from fiber materials having a hollow portion; that is, fiber materials of which at least a part of are hollow. Typically, the hollow fibers are substantially tubular in shape, with openings at each end. The hollow portion of the fiber may run directly through the center of the fiber, or the hollow portion may be partially or substantially off-center. The hollow portion of the fiber typically includes ambient air and generally remains open at each end; that is, the fibers typically remain unsealed at each end so as not to trap air or other gas within the hollow portion of the fiber. The hollow fibers of the present disclosure also have a lower mass per fixed volume than solid fibers or fibers having a lower percentage of hollowness. Accordingly, a greater percent (by weight) of the filler fiber may be included in the nonwoven web of the present disclosure, as compared to conventional nonwoven webs. The higher percentage of filler fiber results in a "bulkier" (i.e., thicker (in z-directional, if x-y is the plane)) nonwoven web. As noted above, bulkiness is a particularly desirable property in the nonwoven web when used in a surge management layer. The hollow fibers typically also have enhanced resiliency due to a larger surface area (i.e., the surface area on the outer surface of the fiber, as well as the surface area within the hollow portion of the fiber). Thus, more stress is required to bend the fiber, and the fiber possesses improved springiness.

One method of determining the hollowness of the filler fiber is by calculating the total cross-sectional area of the fiber and the percentage of the total cross-sectional area of the fiber which is hollow. Looking now to FIG. 1A, a hollow filler fiber 2 is illustrated. The hollow fibers are generally elongate and have a cross-sectional area (1B). As noted in the cut-away portion of filler fiber 2, the fiber includes a hollow portion H. Hollow portion H is surrounded by the fiber material F that forms the fiber itself. Looking now to FIG. 1B, the cross-sectional view of fiber 2 is illustrated. As shown, hollow portion H is surrounded by fiber material F. Suitable fiber materials for use in forming the hollow fibers are described in detail below.

Figure 1B:
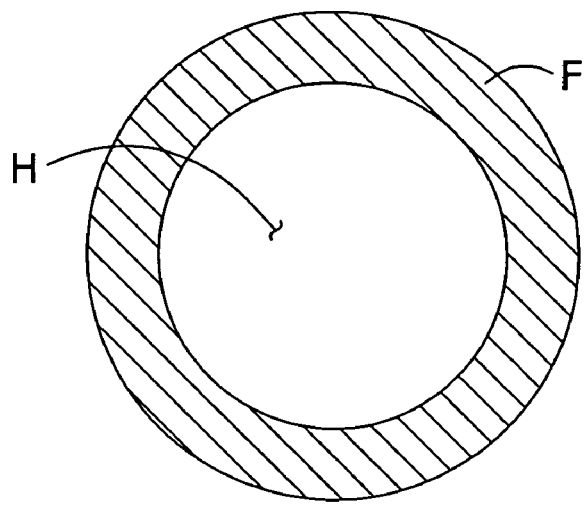
Figure 2A:
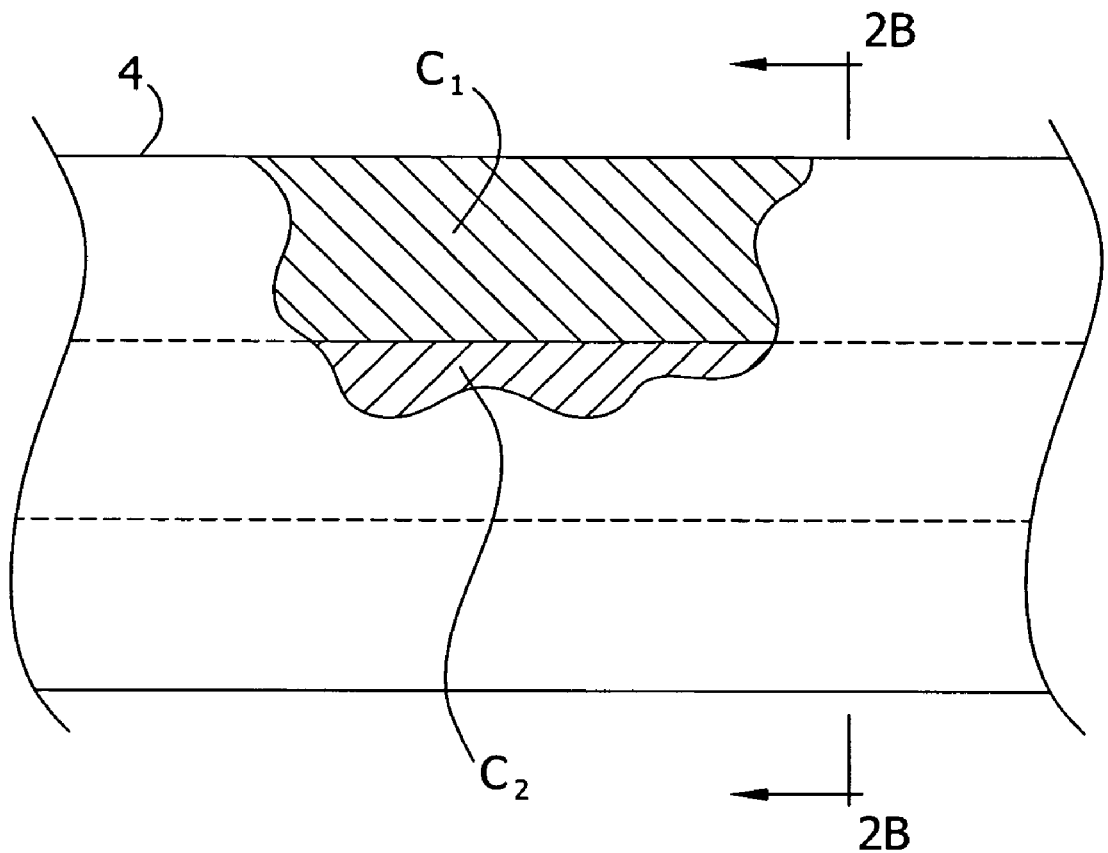
FIGS. 2A and 2B are longitudinal (FIG. 2A) and cross-sectional (FIG. 2B) views of the binder fiber of the present disclosure.
Figure 2B:
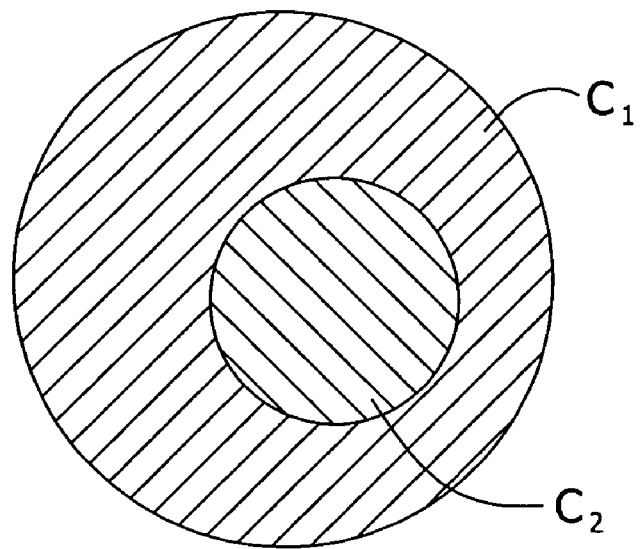

It will be understood by one of skill in the art that although the fiber illustrated in FIGS. 1A and 1B is represented by a perfect cylinder, the actual fibers need not necessarily be as such, and typically are not perfect cylinders. Additionally, although the hollow portion H is shown directly in the center of the fiber in FIG. 1B, it may be partially or substantially off-center. Furthermore, fibers may have various configurations to promote wetability, stiffness, opacity, ease or resistance to slitting, and other properties. Illustrations of simple and complex cross-sectional geometries of synthetic fibers are provided in U.S. Pat. No. 5,069,970 to Largman et al. (FIGS. 1-9); U.S. Pat. No. 6,582,639 to Nellis (FIGS. 6-9); U.S. Pat. No. 6,649,547 to Arnold et al. (FIGS. 2-9); and in "Novel Properties of PLA Fibers", Jeffrey S. Dugan, TAPPI Nonwovens Conference proceedings, 2000, (FIG. 2-10). As illustrated, some fibers have one component, others have more than one component; potentially any of the illustrated fiber shapes may be multicomponent.

The total cross-sectional area of the fiber and the hollow portion of the cross-sectional area of the fiber are typically determined visually, such as with a microscope or other imaging apparatus equipped with a ruler, e.g., using the diameter and/or the radius of the total fiber cross-section and the diameter and/or the radius of the hollow portion.

The filler fiber is from about 5% (by cross-sectional area) to about 50% (by cross-sectional area) hollow. For example, the filler fiber may be at least about 15% (by cross-sectional area) hollow; at least about 25% (by cross-sectional area) hollow; at least about 35% (by cross-sectional area) hollow; or at least about 45% (by cross-sectional area) hollow. In some embodiments, the filler fiber is from about 10% (by cross-sectional area) to about 50% (by cross-sectional area) hollow. For example, the filler fiber may be at least about 20% (by cross-sectional area) hollow; at least about 30% (by cross-sectional area) hollow; or at least about 40% (by cross-sectional area) hollow. Alternatively, the filler fiber is from about 15% (by cross-sectional area) to about 45% (by cross-sectional area) hollow. For example, the filler fiber may be at least about 18% (by cross-sectional area) hollow; at least about 28% (by cross-sectional area) hollow; at least about 32% (by cross-sectional area) hollow; or at least about 42% (by cross-sectional area) hollow.

The degree of hollowness that a given fiber may possess (as represented by percent cross-sectional area) is typically a function of the fiber diameter and the strength of the polymeric material utilized to form the fiber. For example, relatively soft polymers and/or relatively small fiber diameters will result in a fiber having a relatively lower degree of hollowness. Softer polymers are generally less crystalline and tend to flow more readily upon melting to close up or collapse the hollow portion of the fiber. Smaller diameter fibers start out with a smaller cross-sectional diameter, so melting polymers flowing at a constant rate of speed will tend to close up a higher percentage of the hollow portion of the fiber in a fixed amount of time.

The diameter of the filler fiber typically has a diameter of from about 1 micrometer to about 100 micrometers; alternatively, the diameter of the filler fiber is from about 10 micrometers to about 60 micrometers; in another alternative, the diameter of the filler fiber is from about 15 micrometers to about 40 micrometers. For example, the filler fiber may be from about 20 micrometers to about 30 micrometers in diameter. Similar to the degree of hollowness of the filler fiber, the diameter of the filler fiber may be determined visually (e.g., using a microscope or other imaging apparatus equipped with a ruler). It has been found that hollow fibers having diameters within the above ranges possess beneficial attributes such as strength and resiliency when utilized as a filler fiber in a nonwoven web.

One or more of various known methods may be utilized to achieve distinct fiber diameters and/or percent hollowness within the ranges described herein. For example, distinct fiber diameters can be achieved by employing different sized exit orifices or outlet openings in a spinneret, spin plate or die body. Various methods of making hollow fibers are also known in the art such as, for example, by using a plurality of arced exit slots whereby swelling of the fiber material after extrusion causes the molten fiber material to form a fiber having a hollow portion. Generally speaking, any material (e.g., a polymeric material) that is capable of being extruded through one or more arced orifices or outlet openings in a spinneret, spin plate or die body may be utilized to form a hollow fiber.

The filler fiber may have a higher melting temperature than the melting temperature of at least one of the components of the binder fiber, discussed in detail below. Typically, the filler fiber has a melting temperature of from about 120° C. to about 350° C. For example, the melting temperature of the filler fiber may be from about 130° C. to about 300° C. Alternatively, the melting temperature of the filler fiber may be from about 145° C. to about 270° C. As utilized herein, the term "melting temperature" refers to the temperature at which the crystalline portions of the polymer melt. One method of determining the melting temperature, glass transition temperature and degree of crystallinity of a material is by employing differential scanning calorimetry (DSC). Typically, the melting temperature is recorded at the location where the endothermic melt peak occurs. It may also be possible for a polymer to have more than one melt peak, particularly in polymer blends.

A suitable differential scanning calorimeter for determining melting temperatures and other melting parameters can, for example, be provided by a THERMAL ANALYST 2910 Differential Scanning Calorimeter, which has been outfitted with a liquid nitrogen cooling accessory and with a THERMAL ANALYST 2200 (version 8.10) analysis software program, both of which are available from T.A. Instruments Inc. (New Castle, Del.). Alternatively, a substantially equivalent DSC system may be employed.

The filler fiber desirably includes at least one polymeric material. Various polymeric materials may be utilized to form the filler fiber, provided that the polymeric material selected is capable of forming a fiber having a percent hollowness within the ranges described above.

Suitably, the filler fiber is a biodegradable aliphatic polyester having a higher melting temperature than the melting temperature of at least one component of the binder fiber. In some embodiments, the filler fiber is a biodegradable aliphatic polyester having a higher melting temperature than the melting temperature of the sheath component of the binder fiber. Various biodegradable aliphatic polyesters which may be included in the filler fiber include, for example, polyesteramides, modified polyethylene terephtalate, polylactic acid (PLA), terpolymers based on polylactic acid, polyglycolic acid, polyalkylene carbonates (such as polyethylene carbonate), polyhydroxyalkanoates (PHA), polyhydroxybutyrates (PHB), polyhydroxyvalerates (PHV), polyhydroxybutyrate-hydroxyvalerate copolymers (PHBV), homopolymers and copolymers thereof, combinations thereof, and the like. The filler fiber may include polylactic acid (PLA). The term "polylactic acid" generally refers to homopolymers of lactic acid, such as poly(L-lactic acid); poly(D-lactic acid); and poly(DL-lactic acid), as well as copolymers of lactic acid containing lactic acid as the predominant component and a small proportion of a copolymerizable comonomer, such as 3-hydroxybutyrate, caprolactone, glycolic acid, and the like.

Polylactic acid is generally prepared by the polymerization of lactic acid or lactide. As used herein, therefore, the term "polylactic acid" is intended to represent the polymer that is prepared by either the polymerization of lactic acid or lactide. Any known polymerization method, such as polycondensation or ring-opening polymerization, may be used to polymerize lactic acid. In the polycondensation method, for example, L-lactic acid, D-lactic acid, or a mixture thereof is directly subjected to dehydro-polycondensation. In the ring-opening polymerization method, a lactide that is a cyclic dimer of lactic acid is subjected to polymerization with the aid of a polymerization-adjusting agent and catalyst. The lactide may include L-lactide, D-lactide, and DL-lactide (also referred to as meso-lactide, a condensate of L-lactic acid and D-lactic acid). Each of the aforementioned lactides (i.e., L-lactide, D-lactide, and DL-lactide) is a dimer; that is, they are comprised of two lactic acid units. As a result of its chiral center, lactic acid has two different stereochemical isomers; R isomer and S isomer configurations. D-lactide includes two R isomers, L-lactide includes two S isomers, and meso-lactide includes an R isomer and an S isomer. The various isomers may be mixed and polymerized, if necessary, to obtain polylactic acid having any desired composition and crystallinity, described in further detail below. A small amount of a chain-extending agent (e.g., a diisocyanate compound such as described below, an epoxy compound or an acid anhydride) may also be employed to increase the molecular weight of the polylactic acid. Suitably, the weight average molecular weight of the polylactic acid is within the range of about 60,000 to about 1,000,000.

As noted above, lactic acid and lactide are known to be asymmetrical molecules; they have two optical isomers referred to, respectively, as the levorotatory (hereinafter referred to as "L") enantiomer and the dextrorotatory (hereinafter referred to as "D") enantiomer. As a result, by polymerizing a particular enantiomer or by using a mixture of the two enantiomers, it is possible to prepare different polymers that are chemically similar yet which have different properties. In particular, it has been found that by modifying the stereochemistry of a polylactic acid polymer in this manner it is possible to control, for example, the melting temperature, melt rheology, and crystallinity of the polymer. As a result of the ability to control such properties, it is possible to prepare a thermoplastic composition and a single component or multicomponent fiber exhibiting desired melt strength, mechanical properties, softness, and processability properties. In particular, as a result of the ability to control such properties it is possible to form a hollow fiber having the above melting temperature ranges for use as the filler fiber.

Examples of suitable biodegradable aliphatic polyesters that may be utilized in forming the filler fiber include Biomer® (polylactic acid polymer; commercially available from Biomer, Inc., Krailling, Germany), NatureWorks® PLA Resins (polylactic acid polymer; commercially available from NatureWorks® LLC, Minneapolis, Minn.), Biomax® (polyethylene terephthalate polymer; commercially available from E.I. DuPont de Nemours, Wilmington, Del.), and BAK® (polyesteramide polymer, commercially available from Bayer AG, Leverkusen, Germany).

Alternative polymer-based fiber materials which may be utilized in forming the filler fiber include, for example, semisustainable polymeric fibers such as Sorona® (1,3-propanediol terephthalate; commercially available from E.I. DuPont de Nemours, Wilmington, Del.); non-biodegradable fibers such as Corterra® (polytrimethylene terephthalate; commercially available from Shell Chemicals, Houston, Tex.); aromatic polyamides (aramids) such as Kevlar® (commercially available from E.I. DuPont de Nemours, Wilmington, Del.), Twaron® (commercially available from Teijin Twaron BV, Netherlands), and nylon 6 and nylon 6,6-based fibers (commercially available from a variety of sources).

Other man-made fibers which may be utilized in forming the filler fiber include lower alkyl cellulose esters, such as cellulose acetate butyrate (CAB), cellulose acetate propionate (CAP), and triacetate cellulose, as well as wood pulp-based fibers such as rayon, Lyocell, and TenCell (commercially available from a variety of sources). Natural fibers such as plant- or animal-based fibers may also be utilized, such as ramie, kenaf, hemp, pineapple, bamboo, and the like, if suitable.

In one embodiment, the filler fiber includes a polylactic acid (PLA) polymer. As noted above, PLA polymers and/or PLA-based homopolymers and copolymers typically include both the poly(D-lactic acid) enantiomer, the poly(L-lactic acid) enantiomer, or the poly(DL-lactic acid) racemic mixture. PLA polymers of the present disclosure are generally predominantly comprised of the poly(L-lactic acid) enantiomer, but various amounts of the poly(D-lactic acid) enantiomer are also present. The poly(D-lactic acid) enantiomer possesses an altered constellation (tacticity) of methyl groups, resulting in a disruption in the polymeric crystalline lattice. Consequently, the melting temperature decreases with an increasing poly(D-lactic acid) enantiomer concentration in the polylactic acid polymer.

The melting temperature of an enantiomerically pure PLA polymer, such as pure poly(L-lactic acid), is about 173° C. Less enantiomerically pure PLA will generally have a lower melting temperature. For example, a poly(L-lactic acid) containing from about 1.3% to about 2.0% (by weight) of the D enantiomer, generally has a melting temperature in the range of from about 160° C. to about 170° C. Racemic polylactides (i.e., PLA with about equal fractions of randomly distributed L and D enantiomers) are typically either amorphous or semi-crystalline, and generally have a melting temperature of from about 130° C. to about 140° C. One method of determining the D:L enantiomer ratio is by using liquid chromatography, described below. The melting temperature may be predicted based on D-lactide concentration according to the methods described in, for example, Huang, Runt et al., Macromolecules 1998, 31, 2593-2599 and Baratian, Runt et al., Macromolecules 2001, 34, 4857-4864. Conversely, the D:L composition of a PLA polymer may be estimated based on its melting temperature.

Alternatively, PLA stereocomplexes are blends of approximately equal amounts of poly(D-lactic acid) with poly(L-lactic acid), and generally have melting temperatures in the range of from about 220° C. to about 230° C.; higher than would typically be expected from their D:L composition. Such polylactide stereocomplexes and synthetic methods are described in U.S. Pat. No. 4,719,246 to Murdoch et al.; U.S. Pat. No. 4,766,182 to Murdoch et al.; U.S. Pat. No. 4,800,219 to Murdoch et al.; U.S. Pat. No. 4,902,515A to Loomis et al.; U.S. Pat. No. 4,981,696A to Loomis et al.; and U.S. Pat. No. 5,317,064A to Spinu.

Suitably, when the filler fiber includes a PLA polymer, the amounts of the poly(D-lactic acid) enantiomer and the poly(L-lactic acid) enantiomer are such that the filler fiber has a melting temperature of from about 120° C. to about 350° C. The filler fiber may include enantiomerically pure PLA. In other embodiments, the filler fiber may include PLA including from about 0.1% to about 3.0% (by weight) poly(D-lactic acid) enantiomer. Alternatively, the filler fiber includes polylactic acid including from about 1.0% to about 2.0% (by weight) poly(D-lactic acid) enantiomer. Examples of suitable polylactic acid polymers for use in the filler fiber include NatureWorks® PLA 6201D and Biomer L9000. Alternatively, fibers made of PLA stereocomplexes may be included in the filler fiber.

While the filler fiber will generally substantially comprise a polymeric material such as those described above, the filler fiber is not limited thereto and can include other materials not adversely affecting the desired properties of the filler fiber. Exemplary materials which could be used as additional materials include, for example, other polymers, pigments, antioxidants, stabilizers, surfactants, waxes, flow promoters, solid solvents, particulates, and the like. If such additional materials are included in the filler fiber, it is generally desired that such additional materials be used in an amount that is beneficially less than about 50 weight percent, more beneficially less than about 25 weight percent, and suitably less than about 10 weight percent, wherein all weight percents are based on the total weight amount of the filler fiber.

Additionally or alternatively, the polymers suitable for use in the filler fiber may be modified according to various methods known to those of skill in the art. For example, the polymers may be modified using a fiber finish to remove and/or reduce the presence of static electricity during mechanical processing and/or collection of the fibers. As is known in the art, fiber finish is typically applied during the fiber manufacturing process in two steps. The conventional two-step process includes applying a spin finish, which typically includes an anti-static agent and a lubricant, and a draw finish, which typically includes a hydrophilic component and a lubricant. Methods of applying the spin finish and the draw finish include, for example, using a kiss roller, spraying, dipping, and the like. If present, the fiber finish is generally included in the filler fiber at a concentration of from about 0.2% (by weight filler fiber) to about 0.5% (by weight filler fiber). Of this amount of fiber finish, typically less than about 0.1% (by weight fiber finish) is the spin finish, and typically greater than about 0.2% (by weight fiber finish) is the draw finish. Filler fibers including fiber finishes are well known in the art, and fiber finishes are commercially available from a variety of sources. Additionally, in hygiene-related applications (such as diapers, wipes, and/or feminine pads) the polylactic acid fibers may be modified by the addition of a hydrophilic treatment to enhance the liquid intake properties of the fibers.

II. The Binder Fiber

In addition to the filler fiber, the nonwoven web includes a binder fiber. Generally speaking, the binder fiber is a multicomponent fiber. As utilized herein, the term "multicomponent fiber" generally refers to fibers which have been formed from at least two different polymers extruded from separate extruders but spun together to form one fiber. Multicomponent fibers are also sometimes referred to as conjugate fibers or bicomponent fibers. The two or more polymers that comprise the multicomponent fibers are arranged in substantially constantly positioned distinct zones across the cross-section of the multicomponent fibers and extend continuously along the length of the multicomponent fibers. The configuration of such a multicomponent fiber may be, for example, a sheath/core arrangement wherein one polymer is surrounded by another, or may be a side-by-side arrangement, a pie arrangement, or an "islands-in-a-sea" arrangement.

Methods for making multicomponent fibers are well known and need not be described here in detail. To form a multicomponent fiber, generally, at least two polymers are extruded separately and fed to a polymer distribution system where the polymers are introduced into a segmented spinneret plate. The polymers follow separate paths to the fiber spinneret and are combined in a spinneret hole which comprises either at least two concentric circular holes thus providing a sheath/core type fiber or a circular spinneret hole divided along a diameter into at least two parts to provide a side-by-side type fiber. The combined polymer filament is then cooled, solidified, and drawn, generally by a mechanical rolls system, to an intermediate filament diameter and collected. Subsequently, the filament may be "cold drawn" at a temperature below its softening temperature, to the desired finished fiber diameter and crimped or texturized and cut into a desirable fiber length. Multicomponent fibers can be cut into relatively short lengths, such as staple fibers which generally have lengths in the range of about 25 to about 50 millimeters and short-cut fibers which are even shorter and generally have lengths less than about 18 millimeters. See, for example, U.S. Pat. No. 5,336,552 to Strack et al., which is hereby incorporated by reference herein in its entirety.

The nonwoven web comprises from about 20% (by weight nonwoven web) to about 90% (by weight nonwoven web) binder fiber. For example, the nonwoven web may comprise greater than about 25% (by weight nonwoven web) binder fiber; from about 35% (by weight nonwoven web) binder fiber; from about 75% (by weight nonwoven web) binder fiber; or from about 85% (by weight nonwoven web) binder fiber. In some embodiments, the nonwoven web comprises from about 30% (by weight nonwoven web) to about 70% (by weight nonwoven web) binder fiber. For example, the nonwoven web may comprise greater than about 40% (by weight nonwoven web) binder fiber; from about 50% (by weight nonwoven web) binder fiber; or from about 60% (by weight nonwoven web) binder fiber. Alternatively, the nonwoven web comprises from about 40% (by weight nonwoven web) to about 60% (by weight nonwoven web) binder fiber. For example, the nonwoven web may comprise greater than about 45% (by weight nonwoven web) binder fiber; or from about 55% (by weight nonwoven web) binder fiber.

The binder fiber includes a sheath component and a core component. The sheath component generally provides an exposed surface on at least a portion of the binder fiber which will permit thermal bonding of the binder fiber to other fibers which may be the same or different from the binder fiber (e.g., the filler fiber). As a result, the binder fiber can then be used to form thermally bonded fibrous nonwoven structures such as the nonwoven webs of the present disclosure.

The core component generally provides strength and/or rigidity to the binder fiber and, thus, to any nonwoven web structure comprising the binder fiber. Such strength and/or rigidity to the binder fiber is generally achieved by having the core component have a thermal melting temperature greater than the thermal melting temperature of the sheath component, discussed in further detail below. As a result of the difference in melting temperatures of the sheath and core components, when the binder fiber is subjected to an appropriate temperature, typically greater than the melting temperature of the sheath component but less than the melting temperature of the core component, the sheath component will melt while the core component will generally maintain its rigid form.

Although the melting temperatures of the sheath and core components are generally not as critical as the relative comparison between the two temperatures, it is generally desired that the melting temperatures of the sheath and core components be within a range that is typically encountered in most useful applications. As such, it is generally desired that the melting temperatures of the sheath and core components each preferably be between about 25° C. and about 350° C., more preferably between about 40° C. and about 300° C., still more preferably between about 45° C. and about 275° C.

The "sheath" component of the binder fiber must be at least partially exposed on the surface of the binder fiber. By way of example, the sheath component and the core component may be oriented in a sheath/core configuration (see also, e.g., FIGS. 2A and 2B). Alternatively, the binder fiber may have a side-by-side configuration with the sheath component on one side of the fiber and the core component on the other side of the fiber. In yet other embodiments, the binder fiber may have a complex geometry with the sheath component being at least partially exposed.

The relative amounts of the components in the binder fiber may be determined by calculating the total cross-sectional area of the fiber and the percentage of the total cross-sectional area comprising the sheath component and the core component. Looking now to FIG. 2A, a binder fiber 4 is shown. The multicomponent binder fibers of the present disclosure are generally elongate and have a cross-sectional area (2B). As noted in the cut-away portion of fiber 4, the binder fiber includes a component $C_1$, and a component $C_2$. Although the component $C_1$ and the component $C_2$ are illustrated in a sheath/core configuration, this need not necessarily be the case. Additionally, although the component $C_2$ is shown off-center of the fiber, it may be directly or substantially directly in the center of the fiber.

Similar to degree of hollowness of the filler fiber, the relative amounts of the sheath component and the core component in the binder fiber may be determined visually, such as with a microscope or other imaging apparatus equipped with a ruler, e.g., using the diameter and/or the radius of the total fiber cross-section and the diameter and/or the radius of the component portions.

The binder fiber desirably comprises from about 10% (by cross-sectional area) to about 70% (by cross-sectional area) sheath component. For example, the binder fiber may comprise at least about 25% (by cross-sectional area) sheath component; at least about 40% (by cross-sectional area) sheath component; or at least about 60% (by cross-sectional area) sheath component. In some embodiments, the binder fiber comprises from about 30% (by cross-sectional area) to about 60% (by cross-sectional area) sheath component. For example, the binder fiber may comprise at least about 35% (by cross-sectional area) sheath component; at least about 45% (by cross-sectional area) sheath component; or at least about 55% (by cross-sectional area) sheath component. Alternatively, the binder fiber comprises from about 45% (by cross-sectional area) to about 55% (by cross-sectional area) sheath component. For example, the binder fiber may comprise at least about 48% (by cross-sectional area) sheath component; or at least about 52% (by cross-sectional area) sheath component.

The binder fiber desirably comprises from about 30% (by cross-sectional area) to about 90% (by cross-sectional area) core component. For example, the binder fiber may comprise at least about 40% (by cross-sectional area) core component; at least about 60% (by cross-sectional area) core component; or at least about 80% (by cross-sectional area) core component. In some embodiments, the binder fiber comprises from about 40% (by cross-sectional area) to about 70% (by cross-sectional area) core component. For example, the binder fiber may comprise at least about 45% (by cross-sectional area) core component; at least about 55% (by cross-sectional area) core component; or at least about 65% (by cross-sectional area) core component. Alternatively, the binder fiber comprises from about 45% (by cross-sectional area) to about 55% (by cross-sectional area) core component. For example, the binder fiber may comprise at least about 48% (by cross-sectional area) core component; at least about 50% (by cross-sectional area) core component; or at least about 52% (by cross-sectional area) core component.

A. The Sheath Component

As noted above, the binder fiber may include a sheath component having a lower melting temperature than the melting temperature of the core component of the binder fiber. Suitably, the sheath component has a melting temperature of from about 50° C. to about 260° C. For example, the melting temperature of the sheath component may be from about 80° C. to about 200° C. Alternatively, the melting temperature of the sheath component may be from about 90° C. to about 180° C.

The melting temperature of the sheath component is typically at least about 10° C. lower than the melting temperature of the core component. For example, the melting temperature of the sheath component may be at least about 20° C. lower than the melting temperature of the core component. Alternatively, the melting temperature of the sheath component may be at least about 30° C. lower than the melting temperature of the core component. In another alternative, the melting temperature of the sheath component may be at least about 40° C. lower than the melting temperature of the core component. In yet another alternative, the melting temperature of the sheath component may be at least about 50° C. lower than the melting temperature of the core component.

The melting temperature of the sheath component is also typically at least about 10° C. lower than the melting temperature of the filler fiber. For example, the melting temperature of the sheath component may be at least about 20° C. lower than the melting temperature of the filler fiber. Alternatively, the melting temperature of the sheath component may be at least about 30° C. lower than the melting temperature of the filler fiber. In another alternative, the melting temperature of the sheath component may be at least about 40° C. lower than the melting temperature of the filler fiber. In yet another alternative, the melting temperature of the sheath component may be at least about 50° C. lower than the melting temperature of the filler fiber.

The sheath component generally includes at least one polymeric material. Suitably, the sheath component is a biodegradable aliphatic polyester having a lower melting temperature than the core component. The biodegradable aliphatic polyester in the sheath component may also have a lower melting temperature than the filler fiber. Various biodegradable aliphatic polyesters which may be included in the sheath component include, for example, aliphatic polyesters with repeating units of at least 5 carbon atoms (e.g., polyhydroxyvalerate, polyhydroxybutyrate-hydroxyvalerate copolymer and polycaprolactone), and succinate-based aliphatic polymers (e.g., polybutylene succinate, polybutylene succinate adipate, and polyethylene succinate). More specific examples may include polyethylene oxalate, polyethylene malonate, polyethylene succinate, polypropylene oxalate, polypropylene malonate, polypropylene succinate, polybutylene oxalate, polybutylene malonate, polybutylene succinate, polyethylenedecane dioate and polyethylenetridecane dioate and copolymers of these compounds and a diisocyanate or a lactide. Among these compounds, polybutylene succinate and copolymers thereof are normally preferred.

Exemplary aliphatic polyesters are typically synthesized through the condensation polymerization of a polyol and an aliphatic dicarboxylic acid or an anhydride thereof. The polyols may be substituted or unsubstituted, linear or branched, polyols selected from polyols containing 2 to about 8 carbon atoms, polyalkylene ether glycols containing 2 to 8 carbon atoms, and cycloaliphatic diols containing about 4 to about 12 carbon atoms. Substituted polyols typically contain 1 to about 4 substituents independently selected from halo, $C_6$-$C_{10}$ aryl and $C_1$-$C_4$ alkoxy. Examples of polyols that may be used include, but are not limited to, ethylene glycol, diethylene glycol, propylene glycol, 1,3-propanediol, 2,2-dimethyl-1,3-propanediol, 1,3-butanediol, 1,4-butanediol, 1,5-pentanediol, 1,6-hexanediol, polyethylene glycol, diethylene glycol, 2,2,4-trimethyl-1,6-hexanediol, thiodiethanol, 1,3-cyclohexanedimethanol, 1,4-cyclohexanedimethanol, 2,2,4,4-tetramethyl-1,3-cyclobutanediol, triethylene glycol, and tetraethylene glycol. Preferred polyols include 1,4-butanediol; 1,3-propanediol; ethylene glycol; 1,6-hexanediol; diethylene glycol; 1,4-cyclohexanedimethanol; and the like. Representative aliphatic dicarboxylic acids that may be used include substituted or unsubstituted, linear or branched, non-aromatic dicarboxylic acids selected from aliphatic dicarboxylic acids containing 2 to about 12 carbon atoms and cycloaliphatic dicarboxylic acids containing about 5 to about 10 carbon atoms. The substituted non-aromatic dicarboxylic acids will typically contain 1 to about 4 substituents selected from halo, $C_6$-$C_{10}$ aryl, and $C_1$-$C_4$ alkoxy. Non-limiting examples of aliphatic and cycloaliphatic dicarboxylic acids include malonic, succinic, glutaric, adipic, pimelic, azelaic, sebacic, fumaric, 2,2-dimethyl glutaric, suberic, 1,3-cyclopentanedicarboxylic, 1,4-cyclohexanedicarboxylic, 1,3-cyclohexanedicarboxylic, diglycolic, itaconic, maleic, and 2,5-norbornanedicarboxylic. The polymerization is typically catalyzed by a catalyst, such as a titanium-based catalyst (e.g., tetraisopropyltitanate, tetraisopropoxy titanium, dibutoxydiacetoacetoxy titanium, or tetrabutyltitanate).

If desired, a diisocyanate chain extender may be reacted with the aliphatic polyester prepolymer to increase its molecular weight. Representative diisocyanates may include toluene 2,4-diisocyanate, toluene 2,6-diisocyanate, 2,4'-diphenylmethane diisocyanate, naphthylene-1,5-diisocyanate, xylylene diisocyanate, hexamethylene diisocyanate ("HMDI"), isophorone diisocyanate and methylenebis(2-isocyanatocyclohexane). Trifunctional isocyanate compounds may also be employed that contain isocyanurate and/or biurea groups with a functionality of not less than three, or to replace the diisocyanate compounds partially by tri-or polyisocyanates. The preferred diisocyanate is hexamethylene diisocyanate. The amount of the chain extender employed is typically from about 0.3 to about 3.5 wt. %, in some embodiments, from about 0.5 to about 2.5 wt. % based on the total weight percent of the polymer.

The aliphatic polyesters included in the sheath component may either be a linear polymer or a long-chain branched polymer. Long-chain branched polymers are generally prepared by using a low molecular weight branching agent, such as a polyol, polycarboxylic acid, hydroxy acid, and so forth. Representative low molecular weight polyols that may be employed as branching agents include glycerol, trimethylolpropane, trimethylolethane, polyethertriols, glycerol, 1,2,4-butanetriol, pentaerythritol, 1,2,6-hexanetriol, sorbitol, 1,1,4,4-tetrakis (hydroxymethyl) cyclohexane, tris(2-hydroxyethyl) isocyanurate, and dipentaerythritol. Representative higher molecular weight polyols (molecular weight of 400 to 3,000) that may be used as branching agents include triols derived by condensing alkylene oxides having 2 to 3 carbons, such as ethylene oxide and propylene oxide with polyol initiators. Representative polycarboxylic acids that may be used as branching agents include hemimellitic acid, trimellitic (1,2,4-benzenetricarboxylic) acid and anhydride, trimesic (1,3,5-benzenetricarboxylic) acid, pyromellitic acid and anhydride, benzenetetracarboxylic acid, benzophenone tetracarboxylic acid, 1,1,2,2-ethane-tetracarboxylic acid, 1,1,2-ethanetricarboxylic acid, 1,3,5-pentanetricarboxylic acid, and 1,2,3,4-cyclopentanetetracarboxylic acid. Representative hydroxy acids that may be used as branching agents include malic acid, citric acid, tartaric acid, 3-hydroxyglutaric acid, mucic acid, trihydroxyglutaric acid, 4-carboxyphthalic anhydride, hydroxyisophthalic acid, and 4-(beta-hydroxyethyl)phthalic acid. Such hydroxy acids contain a combination of 3 or more hydroxyl and carboxyl groups. Especially preferred branching agents include trimellitic acid, trimesic acid, pentaerythritol, trimethylol propane and 1,2,4-butanetriol.

Polycaprolactone polymers may also be included in the sheath component. Polycaprolactone polymers are generally prepared by the polymerization of ϵ-caprolactone, which is a seven-member ring compound that is characterized by its reactivity. Cleavage usually takes place at the carbonyl group. Higher molecular weight polycaprolactone may be prepared under the influence of a wide variety of catalysts, such as aluminum alkyls, organometallic compositions, such as Group IA, IIA, IIB, or IIIA metal alkyls, Grignard reagents, Group II metal dialkyls, calcium or other metal amides or alkyl amides, reaction products of alkaline earth hexamoniates, alkaline oxides and acetonitrile, aluminum trialkoxides, alkaline earth aluminum or boron hydrides, alkaline metal or alkaline earth hydrides or alkaline metals alone. An initiator may also be used in the preparation of polycaprolactone, such as an aliphatic diol that forms a terminal end group. Examples of polycaprolactone polymers that may be suitable for use in the sheath component include a variety of polycaprolactone polymers that are available from The Dow Chemical Company, Midland, Mich., such as TONE™ P767E and TONE™ P787.

In one embodiment, the sheath component includes a polylactic acid polymer. In another embodiment, each of the filler fiber and the sheath component of the binder fiber include a polylactic acid polymer. In another embodiment, each of the filler fiber, the sheath component of the binder fiber, and the core component of the binder fiber include a polylactic acid polymer. As described in detail above, polylactic acid generally refers to homopolymers of lactic acid, such as poly(L-lactic acid); poly(D-lactic acid); and poly(DL-lactic acid), as well as copolymers of lactic acid containing lactic acid as the predominant component and a small proportion of a copolymerizable comonomer, such as 3-hydroxybutyrate, caprolactone, glycolic acid, and the like.

In the present disclosure, when each of the sheath component and the core component of the binder fiber include a polylactic acid polymer, it is desired that the sheath component have a greater amount of the poly(D-lactic acid) enantiomer than the amount of poly(D-lactic acid) enantiomer in the core component. As noted above, this is because the L:D ratio generally determines the limits of a polymer's intrinsic crystallinity which in turn generally determines the melting temperature of a polymer. The degree of crystallinity of a polylactic acid polymer is based on the regularity of the polymer backbone and its ability to line up with similarly shaped sections of itself or other chains. If even a relatively small amount of the poly(D-lactic acid) enantiomer (of either lactic acid or lactide), such as about 1.5 to about 12 weight percent, is copolymerized with the poly(L-lactic acid) enantiomer (of either lactic acid or lactide), the polymer backbone generally becomes irregularly shaped enough that it cannot line up and orient itself with other backbone segments of pure L-enantiomer polymer. Therefore, the polylactic acid polymer in the sheath component, comprising more D-enantiomer, will be less crystalline than the polylactic acid polymer in the core component and will have a lower melting temperature.

Suitably, when the sheath component includes a polylactic acid polymer, the amounts of poly(D-lactic acid) and poly(L-lactic acid) enantiomers are preferably such that the sheath component has a melting temperature of from about 50° C. to about 260° C. Preferably, the sheath component includes a polylactic acid polymer including from about 3% (by weight) to about 10% (by weight) poly(D-lactic acid) enantiomer. More preferably, the sheath component includes a polylactic acid polymer including from about 3% (by weight) to about 7% (by weight) poly(D-lactic acid) enantiomer. Examples of suitable polylactic acid polymers for use in the sheath component include NatureWorks® PLA 6350D and 6301D, which have melting temperatures of about 150° C. and 132° C., respectively.

While the sheath component will generally substantially comprise a polymeric material such as those described above, the sheath component is not limited thereto and can include other materials not adversely affecting the desired properties of the sheath component. Exemplary materials which could be used as additional components include, for example, other polymers, pigments, antioxidants, stabilizers, surfactants, waxes, flow promoters, solid solvents, particulates, and materials added to enhance processability of the sheath component. If such additional materials are included in the sheath component, it is generally desired that such additional materials be used in an amount that is beneficially less than about 50 weight percent, more beneficially less than about 25 weight percent, and suitably less than about 10 weight percent, wherein all weight percents are based on the total weight amount of the sheath component.

By way of example, the sheath component may be modified using a fiber finish to remove and/or reduce the presence of static electricity during mechanical processing and/or collection of the fibers, described in detail above. Additionally, in hygiene-related applications (such as diapers, wipes, and/or feminine pads) the sheath component may be modified by the addition of a hydrophilic treatment to enhance the liquid intake properties of the fibers, also described in detail above.

By way of another example, the sheath component may also be optionally modified with one or more additional polymers to improve various properties of the sheath component. For example, the sheath component may additionally include polyethylene glycol or other polyol to reduce the melt viscosity of the sheath component when being melted. When the web is heated to the melting temperature of the sheath component, the sheath will begin to flow along the higher melting temperature (i.e., unmelted) core component. At the positions where one multicomponent binder fiber touches another multicomponent binder fiber, the melted sheath component of each fiber will coalesce into a unified structure that captures both fibers at the point of physical contact, forming a fiber network. At these positions of physical contact the melting polymers may have a tendency to become immobilized and form a meniscus due to enhanced capillarity as a result of multifiber proximity. These menisci then solidfy as "globs" or droplets at the fiber intersections. Using polyethylene glycol or other polyol to reduce the melt viscosity of the sheath component can improve the quality of the fiber-to-fiber bonds and may substantially prevent immobilization and/or the formation of menisci.

In one embodiment, the sheath component additionally includes a polyethylene glycol having an average molecular weight of from about 2,000 to about 10,000. The molecular weight selection of the polyethylene glycol is generally based in the need to optimize the viscosity reduction with phase compatibility and ease of extrusion through conventional fiber spinning methods. In a particularly preferred embodiment, the sheath component additionally includes a polyethylene glycol having an average molecular weight of about 3,400. Examples of suitable polyethylene glycols include Carbowax® (commercially available from Dow Chemical Co., Midland, Mich.) and Carbopol® (commercially available from Noveon, Inc., Cleveland, Ohio).

Other melt viscosity-reducing agents and/or adhesive agents may also be optionally added to the sheath component. For example, low-melt copolyester and copolyamides may be added to the sheath component such as, for example, Griltex® D-15734E and Griltex® D-1299A (commercially available from EMS Griltex, Sumter, S.C.). Thermoplastic copolyester elastomers may also be added to the sheath component such as, for example, Hydrel® (commercially available from E.I. DuPont de Nemours, Wilmington, Del.), Riteflex®, (commercially available from Celanese Corp., Dallas, Tex.), and Arnitel® (commercially available from DSM, Netherlands). Hot-melt adhesives including aliphatic copolyesters may also be added to the sheath component as a blending agent such as those available from Bostik Findley, Inc. (Middletown, Mass.) under the designation PE75, PE85, and PE103.

B. The Core Component

As noted above, the binder fiber also includes a core component having a higher melting temperature than the melting temperature of the sheath component. Suitably, the core component has a melting temperature of from about 120° C. to about 350° C. For example, the melting temperature of the core component may be from about 130° C. to about 300° C. Alternatively, the melting temperature of the core component may be from about 145° C. to about 270° C.

The core component generally includes at least one polymeric material. Suitably, the core component is a biodegradable aliphatic polyester having a higher melting temperature than the melting temperature of the sheath component. Generally speaking, the biodegradable aliphatic polyester for use in the core component may be selected from the same group of biodegradable aliphatic polyesters as those suitable for use in the filler fiber. For example, suitable biodegradable aliphatic polyesters which may be included in the core component include polyesteramides, modified polyethylene terephtalate, polylactic acid (PLA), terpolymers based on polylactic acid, polyglycolic acid, polyalkylene carbonates (such as polyethylene carbonate), polyhydroxyalkanoates (PHA), polyhydroxybutyrates (PHB), polyhydroxyvalerates (PHV), and polyhydroxybutyrate-hydroxyvalerate copolymers (PHBV) homopolymers and copolymers thereof, combinations thereof, and the like. These aliphatic polyesters may be synthesized as described in detail above.

In one embodiment, the core component includes a polylactic acid polymer. Examples of suitable polylactic acid polymers for use in the core component include Nature-Works® PLA 6201D and 6202D, which have melting temperatures of about 164° C. and 160° C., respectively.

In the present disclosure, when each of the sheath component and the core component of the binder fiber include a polylactic acid polymer, it is desired that the core component have a lower amount of the poly(D-lactic acid) enantiomer than the amount of poly(D-lactic acid) enantiomer in the first sheath compound. As discussed in detail above, the ratio of L:D enantiomers of polylactic acid generally determine the limits of the polymer's intrinsic crystallinity, which in turn generally determines the melting temperature of the polymer.

Suitably, when the core component includes a polylactic acid polymer, the amounts of the poly(D-lactic acid) and poly(L-lactic acid) enantiomers are preferably such that the core component has a melting temperature of from about 120° C. to about 350° C. Preferably, the core component includes a polylactic acid polymer including from about 1.0% (by weight) to about 2.5% (by weight) poly(D-lactic acid) enantiomer. More preferably, the core component includes a polylactic acid polymer including from about 1.3% (by weight) to about 2.0% (by weight) poly(D-lactic acid) isomer. The melting temperature of a polylactic acid polymer having a poly(D-lactic acid) enantiomer content of from about 1.3% (by weight) to about 2.0% (by weight) will generally be from about 160° C. to about 170° C. Examples of suitable polylactic acid polymers for use in the core component include NatureWorks® PLA 6201D.

While the core component will generally substantially comprise a polymeric material such as those described above, the core component is not limited thereto and can include other materials not adversely affecting the desired properties of the core component. Exemplary materials which could be used as additional components include, for example, other polymers, pigments, antioxidants, stabilizers, surfactants, waxes, flow promoters, solid solvents, particulates, and materials added to enhance processability of the core component. If such additional materials are included in the core component, it is generally desired that such additional materials be used in an amount that is beneficially less than about 50 weight percent, more beneficially less than about 25 weight percent, and suitably less than about 10 weight percent, wherein all weight percents are based on the total weight amount of the core component.

III. Methods of Making the Nonwoven Webs

The processes used to form the nonwoven web using the various fibers (and components and amounts thereof) described above will result in a material which is very bulky and resilient. Suitable processes for making nonwoven webs are known in the art and include, for example, airlaying, spunbonding, and bonded carded web formation processes.

The bonded carded web process generally refers to webs that are made from staple fibers. The staple fibers are sent through a combing or carding unit, which separates or breaks apart and aligns the staple fibers in the machine direction to form a generally machine direction-oriented fibrous nonwoven web. Such fibers are usually purchased in bales which are placed in an opener/blender or picker which separates the fibers prior to the carding unit.

The fibers formed from the aforementioned polymers may be short staple length fibers such as are used in the airlaying and the bonding and carding processes or longer more continuous fibers as are formed in, for example, the spunbond process. Typical fiber lengths will range between about 6 millimeters and about 74 millimeters; more preferably between about 18 millimeters and about 64 millimeters; most preferably between about 25 millimeters and about 51 millimeters. Lengths outside this range may also be used. By way of example, airlaying typically involves using fibers with lengths in the range of about 6 to about 19 millimeters.

In order to achieve the bulky structure of the nonwoven web of the present disclosure, it may be desirable to crimp the fibers. Crimping can be imparted both mechanically and chemically thereby forming both zig zag or saw tooth and helically or spirally crimped fibers.

The first step in making the nonwoven webs involves massing the fibers and blending them in the desired weight ratio. The fibers are then put through an opening process which opens the tightly grouped fibers and blends the two or more different types of fibers. This opening process consists of a machine which separates the fibers through the use of a picker. These blended fibers are then distributed into a flat layer called a batt. The fiber batt is fed to the carding or combing process which separates and orients the fibers in the machine direction. The card is a large rotating drum with teeth to work the fibers. The carded fibers are then stripped off the card and released in a continuous sheet that is transported by a forming belt.

Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calendar rolls or ultrasonic bonding equipment are used to bond the fibers together, usually in a localized bond pattern, though the web can be bonded across its entire surface if so desired. Another suitable and well-known bonding method, particularly when using conjugate staple fibers, is through-air bonding. Other methods include hydroentanglement, and calendar bonding. To produce the lofty structure desired for surge materials, through-air bonding is usually the preferred method. Through-air bonding involves subjecting the web to a flow of heated air that penetrates through the web. This air should be hot enough to soften or melt the sheath component of the binder fiber, while leaving the core component of the binder fiber intact. The desired air temperature will depend upon the type and amounts of the materials used. For example, the temperature should not be so high that it melts the filler fiber and/or the core component of the binder fiber. Moreover, a higher temperature would likely be required to ensure adequate bonding if the composition contains a small amount of the binder fiber. Typical temperatures used for through air bonding are within the range of about 120° C. to 170° C. (248° F. to 338° F.).

The resultant fibrous nonwoven web will generally be a homogenous single layer blend of whatever type fibers are chosen. It is also possible, however, to form multilayer structures provided they meet the parameters set forth with respect to the present disclosure. Methods for forming multilayer nonwoven webs are well known in the art.

The nonwoven webs of the present disclosure are suited for use as the surge management layer in absorbent articles including disposable absorbent articles such as diapers, adult incontinent products, and bed pads; in catamenial devices such as sanitary napkins, and tampons; and other absorbent articles such as wipes, bibs, wound dressings, and surgical capes or drapes.

Test Procedures

L:D Polylactic Acid Stereoisomer Ratio

A high pressure liquid chromatograph (HPLC) procedure may be used for the determination of the concentrations of D-enantiomer and L-enantiomer lactic acid in solid poly(lactic acid), to an accuracy of 0.1 percent D-enantiomer lactic acid. One method is through the use of an HPLC with a Chiral penicillamine analytical column and diode array or variable wavelength detector set at 238 nanometers(nm). In sample preparation HPLC grade water is generally used.

First, a system suitability standard is prepared by dissolving 0.2 g (±0.1 g) of a D-L lactic acid syrup (85 percent aqueous solution containing approximately equal amounts of each isomer) in 100 ml water. Next, a quality control standard is made by dissolving 2.2 g (±0.1 g) of L-lactic acid crystals, available from Fluka Inc., greater than 99 percent crystalline, and 0.06 g (±0.1 g) of D-L lactic acid syrup (85 percent aqueous solution) to a 100 ml volumetric flask.

Test samples are prepared by combining 2.20 g (±0.05 g) of solid resin sample with 1.40 g (±0.02 g) reagent grade sodium hydroxide (NaOH) and 50-70 ml of water in a refluxing flask and refluxing until all polymer is consumed which usually takes about 3 hours. The condenser is rinsed down after reflux is complete, detached, and the flask is allowed to cool to room temperature. The solution pH is tested and adjusted to a pH of 4 to 7 with sulfuric acid ($H_2SO_4$). The adjusted solution is then transferred to a 100 ml volumetric flask, rinsed thoroughly with water, and diluted to 100 ml with water and mixed. If the sample preparation is cloudy, it can be filtered through a syringe filter such as a Gelman Acrodisk CR (0.45 micron PTFE) or equivalent.

The experimental method begins by injecting the system suitability standard to insure system equilibration. The quality control standard should be injected at the beginning and end of every sequence and after every five sample preparation injections. Once ready, the sample preparations are injected. The system suitability standard is injected at the end of the sequence. After all samples have been analyzed, the column is washed at 0.2 to 0.5 milliliters per minute for several hours with a clean-up mobile phase.

The final calculations are based on the area of the peaks produced by the HPLC. The approximate retention times are: 20-24 minutes for the D-isomer and 24-30 minutes for the L-isomer. The resolution(R) is 2 times $[(Rt_{L(+)}-Rt_{D(-)}]/[(W_{L(+)}/W_{D(-)}]$, where W is the corrected peak width at the baseline in minutes and Rt is the retention time in minutes. The number of theoretical plates (N) is 16 times $(Rt/W)^2$. The percent D-lactic acid is calculated as the area of the D-lactic acid peak divided by the combined area of the L-lactic acid and D-lactic acid peak with the result then multiplied by 100.

Fiber Tenacity

One method of determining the fiber tenacity and other properties of the fibers is by employing the following tensile testing procedure. First, individual fiber specimens (~10 to 15) are carefully extracted from the staple fiber and placed separately on a black velvet cloth. The fiber specimens are then mounted in a substantially straight condition on a rectangular paper frame having 51 mm×51 mm external dimensions, and 25 mm×25 mm internal dimensions. The ends of each fiber specimen can be operatively attached to the frame by carefully securing the fiber ends to the sides of the frame with adhesive tape. Each fiber specimen can then be measured for its external, relatively shorter, cross-fiber dimension employing a conventional laboratory microscope, which has been properly calibrated and set at 40 times magnification. This cross-fiber dimension is recorded as the diameter of the individual fiber specimen. The frame helps to mount the ends of the sample fiber specimens in the upper and lower grips of a constant rate of extension type tensile tester in a manner that avoids excessive damage to the fiber specimens.

According to this particular method, a constant rate of extension type of tensile tester and an appropriate load cell are employed for the tensile testing. The load cell is chosen (e.g. 10N) so that the test value falls within 10-90% of the full scale load. A suitable tensile tester is a MTS SYNERGY 200 tensile tester, and the tensile tester and appropriate load cell are available from MTS Systems Corporation (Eden Prairie, Minn.). Alternatively, substantially equivalent equipment may be employed. The fiber specimens in the frame assembly are then mounted between the grips of the tensile tester such that the ends of the fibers are operatively held by the grips of the tensile tester. Then, the sides of the paper frame that extend parallel to the fiber length are cut or otherwise separated such that the tensile tester applies the test force only to the fibers. The fibers are then subjected to a pull test at a pull rate and grip speed of 12 inch/min. The resulting data can be analyzed using a TESTWORKS 4 software program from the MTS Systems Corporation (Eden Prairie, Minn.) with the settings shown in Table 1, below.

TABLE 1

| Calculation Inputs | | Test Inputs | |
| --- | --- | --- | --- |
| Name | Value | Name | Value |
| Break Marker Drop | 50% | Break Sensitivity | 90% |
| Break Marker Elongation | 0.1 in | Break Threshold | 10 gf |
| Nominal Gauge Length | 1 in | Data Acq. Rate | 10 Hz |
| Slack Pre-Load | 1 lbf | Denier Length | 9000 m |
| Slope Segment Length | 20% | Density | 1.25 g/cm$^3$ |
| Yield Offset | 0.20% | Initial Speed | 12 in/min |
| Yield Segment Length | 2% | Secondary Speed | 2 in/min |

The tenacity values can be expressed in terms of dynes per denier, or gram-force per denier. The fiber elongation can be expressed in terms of percent elongation (% elongation), as determined at peak load. The conduct of the tenacity test also provides data for the determination of other parameters, such as peak load, Peak Energy, Percent elongation at peak load, and denier. Peak load is the maximum pull force in grams that is exerted by the load cell during the test where eventually the fiber breaks. Percent elongation at peak load is the strain or percent extra length gained by the fiber compared to its initial length (at the onset of test) when maximum pull force is exerted during the course of test.

Basic Weight

To calculate the basis weight of a nonwoven web, a circular sample of 3 inches (7.6 cm) diameter is cut and weighed using a balance. Weight is recorded in grams. The weight is divided by the sample area. Five samples are measured and averaged.

Material Caliper (Thickness)

The caliper of a material is a measure of thickness, which is measured at 0.05 psi (3.5 g/cm$^2$) with a STARRET® bulk tester, in units of inches. Substantially equivalent equipment may also be employed. Samples are cut into 4 inch by 4 inch (10.2 cm by 10.2 cm) squares and five samples are tested and the results averaged.

Void Volume

Void volume can be calculated as the volume of air in cc/g of nonwoven. Thus, for example, it can be calculated by subtracting the volume of pure polymer from a given volume of nonwoven and dividing this value by the weight of nonwoven.

Compressibility

Compressibility is a measure of the nonwoven web's ability to return to its original condition following an applied pressure. One method of measuring compressibility is using a Digimatic Indicator. Substantially equivalent equipment may also be employed. According to this method, the thickness of the sample at applied pressures of 0.2 psi, then 2.0 psi, and then 0.2 psi are measured. The ratio of the thickness at the final measurement to the initial thickness, multiplied by 100 to yield percent, is the Percent Bulk Recovery. This is a particularly important parameter for applications where a product may be subjected to almost the full weight load of the user, for example in a baby diaper or adult incontinence care product.

Fluid Intake and Flowback Evaluation (FIFE)

The horizontal Fluid Intake and Flowback Evaluation (FIFE) determines the intake potential of the articles. The FIFE generally entails insulting the structure by pouring a defined amount of 0.9 percent saline solution into a cylindrical column resting vertically on top of the structure and recording the time it takes for the fluid to be taken in by the structure. The sample to be tested is placed on a flat surface that is 114 mm×114 mm square platform on a 178 mm×178 mm bottom plexiglass square plate and the FIFE testing apparatus is placed on top of the sample. The FIFE testing apparatus consists of a rectangular, 178 mm×178 mm, plexiglass flat piece upon which was centered a cylinder with an inside diameter of 25 mm. The flat piece has a 32 mm hole corresponding with the cylinder so that fluid can pass through it from the cylinder to the sample. The FIFE testing apparatus weighs 0.36 kg (0.8 pounds). The Plexiglas assembly weighs 360 g and Brass weights in shape of rings are placed on it to apply 0.2 psi of pressure.

Intake times are typically recorded in seconds. Samples were cut into 4 by 4 inch (10.1 by 10.1 cm) pledgets and were inserted into a HUGGIES® step 4 diaper as a surge. The samples were then insulted three times at 60 mL per insult at a rate of 15 ml/sec administered by a MASTERFLEX® Digi-Static batch/dispense pump through a 3 mm ID flexible isoprene tubing.

TransEpidermal Water Loss (TEWL)

Skin hydration values are determined by measuring Trans Epidermal Water Loss (TEWL) and can be determined by employing the following test procedure.

The test is conducted on adults on the forearm. Any medications should be reviewed to ensure they have no effect on test results and the subject's forearms should be free of any skin conditions such as rashes or abrasions. Subjects should relax in the test environment, which should be at about 72° F. (22° C.) with a humidity of about 40 percent, for about 15 minutes prior to testing and movement should be kept to a minimum during testing. Subjects should wear short sleeve shirts, not bathe or shower for about 2 hours before testing, and should not apply any perfumes, lotions, powders, etc., to the forearm.

The measurements are taken with an evaporimeter, such as a DERMALAB® instrument distributed by Cortex Technology, Textilvaenget 1 9560 Hadsund Denmark.

A baseline reading should be taken on the subject's forearm and should be less than 10 g/m$^2$/hr. Each test measurement is taken over a period of two minutes with TEWL values taken once per second (a total of 120 TEWL values). The digital output from the Evaporimeter EP1 instrument gives the rate of evaporative water loss (TEWL) in g/m$^2$/hr.

The end of a dispensing tube is placed on the mid-forearm for carrying out the test. The eye of the tube should be facing the target loading zone. A hand-made sample (without elastics or fasting system) for testing is placed on the subject's forearm directly over the end of the tube. The product may vary depending upon the type of material to be tested or material availability so care should be taken to ensure that test results are comparable. A stretchable net such as that available from Zens Industrial Knit Products of Milwaukee, Wis., should be placed over the product to help to hold it in place. Alternatively, the sample may be sealed on the sides with tape on the subject's arm to minimize the possibility of leaking.

Four equal loadings of 45 mL of physiologic saline available from VWR Scientific Products (West Chester, Pa.) at about 95° F. (35° C.) are delivered to the product at an interval of 45 seconds at a rate of 100 mils/minute by a pump such as a MASTERFLEX® Digi-Static batch/dispense pump. After 60 minutes, the product is removed from the subject's forearm and Evaporimeter readings taken immediately on the skin where the product had been.

TransEpidermal Water Loss values are reported as the difference between the one hour and baseline values in g/m$^2$/hr.

The statistical significance (e.g., 95% confidence) of the TEWL data can be determined by inputting the data from each subject and nonwoven web into Standard Statistical Software JMP version 4.0 (available from SAS Institute, Cary, N.C.). One conventional analysis procedure is the one way analysis of means comparison using the Tukey-Kramer HSD method. Alternatively, other substantially equivalent software packages and/or means for calculating statistical significance may be employed.

Lister Test (Liquid Strike-Through Time)

The Lister test is used to determine the liquid strike-through time of a test sample of nonwoven fabric. The strike-through time is the time taken by a specified amount of liquid to be absorbed in the nonwoven fabric. One suitable test procedure is the EDANA test No. 150.9-1 (liquid strike-through time test). According to one method, a 4 inch by 4 inch (10.2 cm×10.2 cm) sample of the selected nonwoven fabric material is weighed and placed on a 4 inch by 4 inch (10.2 cm×10.2 cm) assembly of 5-ply filter paper, type ERT FF3 (available from Hollingsworth and Vose Co., East Walpole, Mass.). The sample assembly is then placed under a Lister tester. A suitable Lister tester is available from W. Fritz Mezger Inc., Spartanburg, S.C. A strike-through plate is employed for the testing, and is positioned over the test sample and under the Lister test equipment. A 5 mL amount of 0.9% saline is delivered onto the sample assembly. The time to absorb the liquid (strike-through time) is measured automatically by the Lister testing equipment and displayed. Subsequently, a new 5-ply blotter assembly is quickly placed underneath the nonwoven sample within 20 seconds, and the 5 mL delivery of saline is repeated. In total, the 5 mL delivery of liquid is performed 5 times on the selected nonwoven sample, and each strike-through time is recorded. The sample is weighed again after the sequence of 5 tests. For a given nonwoven fabric sample, the 5-sequence test is repeated three times, and the 15 results are averaged to provide the strike-through time of the material.

Strip Tensile Tesr for Machine Direction (MD) Peak Load (Tensile Strength) of Nonwovens This test is based on INDA Standard Test IST 110.5 (95) and ASTM D5034-95 & ASTM D5035-95. The direction into which the nonwoven web moves when produced as a carded web is called the Machine Direction (MD) and the direction perpendicular to it is called Cross Direction (CD). The moving nonwoven is collected as a roll and the MD length is generally very long compared to CD of a roll. Due to the general direction of fiber orientation in carding fibers into webs, the MD tensile strength is typically higher than CD. A strip of material is cut using a sharp die in 125 mm long in MD direction and 50 mm wide in CD direction. According to this particular method, a constant rate of extension type of tensile tester and an appropriate load cell are employed for the tensile testing. The load cell is chosen (e.g., 100N) so that the test value falls within 10-90% of the full scale load. A suitable tensile tester is a MTS SYNERGY 200 tensile tester, and the tensile tester and appropriate load cell are available from MTS Systems Corporation (Eden Prairie, Minn.). Alternatively, substantially equivalent equipment may be employed. The nonwoven specimen of above described dimension is then mounted between the grips (25 mm tall and 76 mm long) of the tensile tester such that the ends of the nonwoven are operatively held by the grips of the tensile tester. The grip pneumatic pressure is kept at about 2.8 kg force/CMQ to avoid sample slippage. The shorter side of the nonwoven strip (50 mm wide) is placed in the grips. The tensile tester applies the test force only to the specimen. The specimen is then subjected to a pull test at a pull rate and grip speed of 12 inch/min (0.508 cm/sec); the gauge length, load limit and sample width are specified at 3 inches (7.62 cm), 20 lbf (89 N) and 2 inches (5.08 cm) respectively. The resulting data can be analyzed using a TESTWORKS 4 software program from the MTS Systems Corporation (Eden Prairie, Minn.). The test provides results in the form of Peak Load (gram force) and strain at Peak (%), among others.

Having described the disclosure in detail, it will be apparent that modifications and variations are possible without departing the scope of the disclosure defined in the appended claims. Furthermore, it should be appreciated that all examples in the present disclosure are provided as non-limiting examples.

EXAMPLE 1

In this Example, six nonwoven webs were formed from polylactic acid bicomponent fibers and hollow or solid polylactic acid filler fibers. Table 2 summarizes some of the properties of the fibers that were used. Test methods for obtaining the information presented in Table 2 are described in detail above.

TABLE 2

| | Fiber I.D. | Type | Diam. (μm) | Deiner | Staple (mm) | Tenacity | Peak Load | Elongation at Peak Load (%) |
|---|---|---|---|---|---|---|---|---|
| Binder | C | Bico | 16.6 | 1.5 | 38 | 4.12 | 7.3 | 70.9 |
| | B1 | Bico | 12.5 | 1.5 | 38 | 5.64 | 7.6 | 23.6 |
| | B1A | Bico | 12.5 | 1.5 | 38 | 5.64 | 7.6 | 23.6 |
| Filler | F1 | Solid | 25.4 | 5.5 | 38 | 2.75 | 15.6 | 40 |
| | F2 | Hollow | 27.5 | 4.4 | 38 | 1.1 | 7.3 | 15.08 |
| | F3 | Solid | 13.5 | 1.5 | 38 | 3.81 | 6.1 | 7.6 |

In particular, binder fiber B1 was a bicomponent binder fiber including about 50% (by weight) sheath component and about 50% (by weight) core component. The sheath component of the binder fiber included a polylactic acid polymer including about 4-4.5% (by weight) poly(D-lactic acid) enantiomer (commercially available as PLA resin NatureWorks® 6350D. Binder fiber B1A included the same sheath component as binder fiber B1, however, B1A also included about 5% (by weight) polyethylene glycol in the sheath recipe as a melt enhancer. The core component of binder fibers B1 and B1A included a polylactic acid polymer including about 1.3-1.5% (by weight) poly(D-lactic acid) enantiomer (commercially available as PLA resin NatureWorks® 6201D. Binder fiber C is a commercial bicomponent fiber ESC215 from ES Fibervision including polyolefins. Filler fiber C3 is a fine denier regenerated cellulose TENCEL™ fiber H25963 from Lenzing Inc.

Filler fibers F1 and F2 included the same polylactic acid polymer as the core component in binder fibers B1 and B1A (i.e., (commercially available as PLA resin NatureWorks® 6201D, however, filler fiber F1 was a solid fiber and filler fiber F2 was a hollow fiber. The cross-sectional area of filler fiber F2 was about 23% (by cross-sectional area) hollow.

The polylactic acid binder fibers and filler fibers were massed and blended in the weight ratios indicated in Table 3, below. Nonwoven webs were then formed from the fibers using a conventional bonded carded web process with a through-air bonder temperature of 130° C.-134° C. (266° F.-272° F.).

Table 3 summarizes the nonwoven webs produced and the process conditions used.

TABLE 3

| Nonwoven Web | PLA binder fiber | PLA filler fiber | Wt. Ratio Binder:Filler | Speed (ft/min) | Oven Temp. (° C.) | Oven Hood Pressure (psi) | Peak Load* (g/50 mm) |
|---|---|---|---|---|---|---|---|
| #1 | B1 | F1 | 60:40 | 50 | 130.0 | 0.2 | 5303 |
| #2 | B1A | F2 | 40:60 | 50 | 131.7 | 0.4 | 4251 |
| #3 | B1 | F1 | 60:40 | 50 | 133.3 | 0.9 | 4268 |
| #4 | B1 | F2 | 40:60 | 50 | 133.3 | 0.9 | 4113 |
| #5 | C, B1 | F | 15 + 25:60 | 50 | 132.2 | 0.9 | 4186 |
| #6 | B1 | F3, F2 | 50:20 + 30 | 50 | 135.6 | 0.9 | 3764 |

*Machine direction (MD) strip tensile test of 50 mm wide by 125 mm long samples

As illustrated in Table 3, PLA-based fibers can be mixed with polyolefin based fibers and non-melting regenerated cellulose fibers to form nonwoven webs of adequate tensile strength; that is, a sufficient tensile strength for collecting the nonwovens in roll form, slitting them in stripped rolls, and utilizing them in a diaper from the stripped rolls (see, e.g., nonwoven webs #5 and #6).

Various physical properties of the nonwoven webs produced according to the parameters set forth in Tables 2 and 3 were tested and compared to two control nonwoven webs. Control (1) was a 77 gsm commercial nonwoven web (7.6 cm wide ×21.6 cm long) including a mixture of polyethylene/polypropylene bicomponent binder fibers and polyester solid filler fibers (60% binder:40% filler). Control (2) was a 80 gsm commercially available nonwoven web (2 deiner×51 mm staple) including a mixture of polyethylene/polypropylene bicomponent binder fibers and polyester filler fibers (60% binder:40% filler) (available from SAMBO Company, Daegu, S. Korea). Table 4 summarizes the properties of the four nonwoven webs including polylactic acid fibers and the control nonwoven webs.

TABLE 4

| Properties | PLA Nonwoven Web | | | | Control | |
| | #1 | #2 | #3 | #4 | (1) | Control (2) |
|---|---|---|---|---|---|---|
| Basis weight (gsm) | 72 | 74.5 | 65 | 63 | 73.5 | 90.5 |
| Void volume (cc/gram) | 33.7 | 36.36 | 39.84 | 51.61 | 30.30 | 30.91 |
| Bulk @ 0.05 psi | 0.098 | 0.109 | 0.104 | 0.13 | 0.09 | 0.113 |
| Bulk density (g/cc) | 0.029 | 0.027 | 0.025 | 0.019 | 0.032 | 0.032 |

As illustrated in Table 4, each of the nonwoven webs #1-4 including polylactic acid fibers from Example 1 possessed a higher void volume as compared to the control nonwoven webs which did not include polylactic acid fibers. Additionally, nonwoven web #2 (which included a hollow filler fiber and a lower weight percentage of binder fiber) possessed a higher void volume as compared to nonwoven web #1 (which included a solid filler fiber and a higher weight percentage of binder fiber) when produced under similar processing conditions. Similarly, nonwoven web #4 (which included a hollow filler fiber and a lower weight percentage of binder fiber) possessed a higher void volume as compared to nonwoven web #3 (which included a solid filler fiber and a higher weight percentage of binder fiber) when produced under similar processing conditions. As noted above, higher void volume provides improved fluid transport properties.

EXAMPLE 2

In this Example, a Lister test was performed on the nonwoven webs #1-4 from Example 1 and the control nonwoven webs according to the Lister test method described above. The Lister test was performed on the top side of each nonwoven web and the bottom side of each nonwoven web (i.e., the side facing down during the bonded carded web process). The results of the Lister test are presented in Table 5 (top side) and Table 6 (bottom side), below. In Tables 5, 6, and 7, the standard deviation (±) is calculated based on four samples tested.

TABLE 5

| Nonwoven Web | Basis Weight (gsm) | 1st Insult (sec) | 2nd Insult (sec) | 3rd Insult (sec) | 4th Insult (sec) | 5th Insult (sec) |
|---|---|---|---|---|---|---|
| #1 | 72.0 | 1.47 (±0.246) | 1.467 (±0.147) | 1.593 (±0.165) | 1.68 (±0.087) | 1.883 (±0.05) |
| #2 | 74.5 | 1.41 (±0.075) | 1.493 (±0.235) | 1.667 (±0.101) | 1.807 (±0.038) | 2.05 (±0.061) |
| #3 | 65 | 0.756 (±0.441) | 1.426 (±0.457) | 1.662 (±0.832) | 1.888 (±0.874) | 1.286 (±0.188) |
| #4 | 63 | 0.966 (±0.283) | 1.434 (±0.762) | 1.522 (±0.148) | 1.56 (±0.757) | 1.584 (±0.546) |
| Control (1) | 73.5 | 1.963 (±0.116) | 1.98 (±0.165) | 1.957 (±0.068) | 2.3 (±0.22) | 3.013 (±0.309) |

TABLE 5-continued

| Nonwoven Web | Basis Weight (gsm) | 1st Insult (sec) | 2nd Insult (sec) | 3rd Insult (sec) | 4th Insult (sec) | 5th Insult (sec) |
|---|---|---|---|---|---|---|
| Control (2) | 90.5 | 1.634 (±0.5) | 2.742 (±1.581) | 2.28 (±0.619) | 3.488 (±1.2) | 3.782 (±0.982) |

TABLE 6

| Nonwoven Web | Basis Weight (gsm) | 1st Insult (sec) | 2nd Insult (sec) | 3rd Insult (sec) | 4th Insult (sec) | 5th Insult (sec) |
|---|---|---|---|---|---|---|
| 1 | 72.0 | 1.63 (±0.174) | 1.44 (±0.312) | 1.867 (±0.323) | 1.69 (±0.072) | 1.783 (±0.038) |
| 2 | 74.5 | 1.9 (±0.182) | 1.787 (±0.055) | 1.76 (±0.05) | 1.827 (±0.025) | 2.013 (±0.078) |
| 3 | 65 | 0.01 (±0.022) | 0.328 (±0.546) | 0.602 (±0.518) | 0.612 (±0.468) | 0.824 (±0.291) |
| 4 | 63 | 0.128 (±0.112) | 0.2 (±0.176) | 0.484 (±0.498) | 0.76 (±0.312) | 0.586 (±0.293) |
| Control (1) | 73.5 | 2.407 (±0.375) | 2.627 (±0.738) | 1.963 (±0.217) | 2.173 (±0.18) | 3.217 (±1.47) |
| Control (2) | 90.5 | 1.442 (±0.846) | 2.794 (±1.648) | 2.172 (±1.45) | 2.888 (±1.331) | 3.184 (±0.472) |

As illustrated in Tables 5 and 6, the liquid acquisition time was shorter for each of the nonwoven webs #1-4 including polylactic acid fibers from Example 1 as compared to the control nonwoven webs which did not include polylactic acid fibers. Furthermore, the successive acquisition times for nonwoven webs #1-4 including polylactic acid did not significantly change or increase, whereas the control nonwoven webs exhibited a longer initial acquisition time and a notable increase in acquisition time upon successive insults. As noted above, an important factor in the performance of personal hygiene products is to possess relatively short liquid acquisition times initially and upon successive insults.

EXAMPLE 3

In this Example, the compressibility of the nonwoven webs #1-4 from Example 1 and the control nonwoven webs was measured according to the compressibility test method described above. The raw data for the compressibility test is presented in Table 7, below.

TABLE 7

| Nonwoven Web | Basis weight (gsm) | 0.20 psi load (mm) | 2.0 psi load (mm) | 0.20 psi load (mm) |
|---|---|---|---|---|
| #1 | 72 | 1.8 (±0.10) | 0.7 (±0.03) | 1.3 (±0.05) |
| #2 | 74.5 | 2.2 (±0.08) | 0.9 (±0.05) | 1.6 (±0.05) |
| #3 | 65 | 1.9 (±0.13) | 0.7 (±0.03) | 1.2 (±0.15) |
| #4 | 63 | 2.2 (±0.15) | 0.7 (±0.05) | 1.4 (±0.23) |
| Control (1) | 74 | 1.5 (±0.05) | 0.6 (±0.05) | 1.1 (±0.05) |
| Control (2) | 91 | 1.8 (±0.03) | 0.8 (±0.03) | 1.2 (±0.03) |

The density (g/cc) of the nonwoven web at each load was then calculated from the raw data in Table 7 using the basis weight of the nonwoven web at the thickness at each applied pressure load, i.e., (basis weight)/(thickness)=(density). The difference between the final density (after compression at 2.0 psi) and initial density was then calculated. Density calculations are presented in Table 8, below.

TABLE 8

| Nonwoven Web | Initial Density @ 0.2 psi (g/cc) | Density @ 2.0 psi (g/cc) | Final Density @ 0.2 psi (g/cc) | Final Density minus Initial Density (g/cc) |
|---|---|---|---|---|
| #1 | 0.040 | 0.098 | 0.054 | 0.014 |
| #2 | 0.034 | 0.081 | 0.046 | 0.012 |
| #3 | 0.035 | 0.091 | 0.054 | 0.019 |
| #4 | 0.029 | 0.089 | 0.044 | 0.015 |
| Control (1) | 0.048 | 0.116 | 0.064 | 0.016 |
| Control (2) | 0.050 | 0.108 | 0.073 | 0.023 |

As illustrated in Table 8, the difference between the final density (after compression at 2.0 psi) and the initial density for the nonwoven webs #1-4 from Example 1 is generally lower than that of the control nonwoven webs. Additionally, nonwoven web #2 (which included a hollow filler fiber and a lower weight percentage of binder fiber) possessed improved compressibility characteristics as compared to nonwoven web #1 (which included a solid filler fiber and a higher weight percentage of binder fiber) when produced under similar conditions. Similarly, nonwoven web #4 (which included a hollow filler fiber and a lower weight percentage of binder fiber) possessed improved compressibility characteristics as compared to nonwoven web #3 (which included a solid filler fiber and a higher weight percentage of binder fiber) when produced under similar conditions.

EXAMPLE 4

In this Example, a FIFE test was performed on three diapers according to the FIFE test procedure described above. The three diapers each included a nonwoven web as a surge management layer.

Diaper A was a commercially available Huggies® UltraTrim diaper of Step 3 size. Diaper B was a diaper assembled offline having the standard components (e.g., liner, surge management layer, outcover, laminate, spacer layer, and the like) formed from standard commercial grade nonwovens. Diaper B also had such standard components as fastening devices and a control absorbent. In particular, Diaper B included nonwoven control (1) from the preceding Examples. Diaper C was similar to Diaper B except Diaper C included nonwoven web #2 from the preceding Examples, which included hollow polylactic acid filler fibers (60% by weight) and bicomponet polylactic acid binder fibers (40% by weight).

The results of the FIFE test are presented in Table 9, below

TABLE 9

| | | Intake Times (sec) | | |
|---|---|---|---|---|
| | Trial | Insult 1 | Insult 2 | Insult 3 |
| Diaper A | 1 | 20.7 | 27.4 | 32.5 |
| | 2 | 17.9 | 27.0 | 30.9 |
| | 3 | 17.2 | 24.1 | 29.3 |
| | Avg. | 18.6 (±1.83) | 26.2 (±1.78) | 30.9 (±1.61) |
| Diaper B | 1 | 23.9 | 26.3 | 31.7 |
| | 2 | 25.2 | 30.5 | 33.8 |
| | 3 | 24.9 | 28.3 | 31.5 |
| | Avg. | 24.7 (±0.72) | 28.4 (±2.12) | 32.3 (±1.30) |
| Diaper C | 1 | 18.0 | 17.3 | 20.0 |
| | 2 | 16.1 | 15.8 | 17.8 |
| | 3 | 15.7 | 15.8 | 18.3 |
| | Avg. | 16.6 (±1.25) | 16.3 (±0.85) | 18.7 (±1.11) |

As illustrated in Table 9, Diaper C including nonwoven web #2 from Example 1 exhibited improved successive intake times as compared to control Diapers A and B. As noted above, faster successive intake times are desired for enhanced fluid management properties of personal hygiene

EXAMPLE 5

In this Example, Diapers A, B, and C as described in Example 4 were subjected to a 22-subject TEWL test according to the TEWL test method described above. The results of the TEWL test are presented in Table 10, below.

TABLE 10

| | TEWL | St. Dev. | Statistical Significance (95% confidence) |
|---|---|---|---|
| Diaper A | 31.96 | 4.4 | C |
| Diaper B | 30.05 | 6.88 | BC |
| Diaper C | 25.24 | 4.74 | A |

As illustrated in Table 10, Diaper C including nonwoven web #2 from Example 1 had a statistically significant lower number of TEWL values as compared to control Diapers A and B. As noted above, a lower TEWL value signifies less moisture transfer to the skin, which results in enhanced dryness to the wearer.

What is claimed is:

1. An absorbent article comprising a surge management layer comprising a nonwoven web, the nonwoven web comprising:
   about 60% (by weight nonwoven web) of a filler fiber; and
   about 40% (by weight nonwoven web) of a binder fiber comprising a sheath component and a core component;
   wherein
   the filler fiber is from about 5% (by cross-sectional area) to about 50% (by cross-sectional area) hollow; and
   the binder fiber comprises from about 10% (by cross-sectional area) to about 70% (by cross-sectional area) sheath component;
   wherein the filler fiber and the core component each comprise a polylactic acid polymer, wherein the polylactic acid polymer comprises from about 1.0% (by weight) to about 2.5% (by weight) of poly(D-lactic acid) enantiomer; and,
   wherein the sheath component comprises a polylactic acid polymer and a melt viscosity-reducing agent, wherein the melt viscosity-reducing agent comprises polyethylene glycol.

2. The absorbent article as set forth in claim 1 wherein the filler fiber is from about 10% (by cross-sectional area) to about 50% (by cross-sectional area) hollow.

3. The absorbent article as set forth in claim 2 wherein the filler fiber is from about 15% (by cross-sectional area) to about 45% (by cross-sectional area) hollow.

4. The absorbent article as set forth in claim 1 wherein the binder fiber comprises from about 30% (by cross-sectional area) to about 60% (by cross-sectional area) sheath component.

5. The absorbent article as set forth in claim 1 wherein the binder fiber comprises from about 30% (by cross-sectional area) to about 90% (by cross-sectional area) core component.

6. The absorbent article as set forth in claim 5 wherein the binder fiber comprises from about 40% (by cross-sectional area) to about 70% (by cross-sectional area) core component.

7. The absorbent article as set forth in claim 1 wherein one or more of the filler fiber, the sheath component, and the core component comprises a polymeric material selected from the group consisting of polyesteramide polymers, polyethylene terephthalate polymers, polylactic acid polymers, polyhydroxybutyrate polymers, homopolymers and copolymers thereof, and combinations thereof.

8. The absorbent article as set forth in claim 1 wherein the filler fiber comprises a biodegradable aliphatic polyester having a higher melting temperature than the melting temperature of the sheath component of the binder fiber.

9. The absorbent article as set forth in claim 8 wherein the core component comprises a biodegradable aliphatic polyester having a higher melting temperature than the melting temperature of the sheath component of the binder fiber.

10. The absorbent article as set forth in claim 1 wherein the polylactic acid polymer in the sheath component comprises from about 3% (by weight) to about 10% (by weight) of the poly(D-lactic acid) enantiomer.

11. The absorbent article as set forth in claim 1 wherein the sheath component has a melting temperature of at least about 10° C. lower than the melting temperature of the filler fiber.

12. The absorbent article as set forth in claim 11 wherein the sheath component has a melting temperature of at least about 10° C. lower than the melting temperature of the core component.

13. The absorbent article as set forth in claim 1 wherein the filler fiber has a melting temperature of from about 120° C. to about 350° C.

14. The absorbent article as set forth in claim 1 wherein the sheath component has a melting temperature of from about 50° C. to about 260° C.

15. The absorbent article as set forth in claim 1 wherein the core component has a melting temperature of from about 120° C. to about 350° C.

16. The absorbent article as set forth in claim 1 wherein the filler fiber further comprises an additional material selected from the group consisting of other polymers, pigments, antioxidants, stabilizers, surfactants, waxes, flow promoters, solid solvents, particulates, materials added to enhance processability, and combinations thereof.

17. The absorbent article as set forth in claim 1 wherein the sheath component further comprises an additional material selected from the group consisting of other polymers, pigments, antioxidants, stabilizers, surfactants, waxes, flow promoters, solid solvents, particulates, materials added to enhance processability, and combinations thereof.

18. The absorbent article as set forth in claim 1 wherein the sheath component further comprises an adhesive agent.

19. The absorbent article as set forth in claim 1 wherein the core component further comprises an additional material selected from the group consisting of other polymers, pigments, antioxidants, stabilizers, surfactants, waxes, flow promoters, solid solvents, particulates, materials added to enhance processability, and combinations thereof.

* * * * *

UNITED STATES PATENT AND TRADEMARK OFFICE
CERTIFICATE OF CORRECTION

PATENT NO. : 7,790,640 B2
APPLICATION NO. : 11/387314
DATED : September 7, 2010
INVENTOR(S) : Jayant Chakravarty et al.

Page 1 of 1

It is certified that error appears in the above-identified patent and that said Letters Patent is hereby corrected as shown below:

In the Specification

In Column 23, Line 32, delete "Tesr" and insert -- Test -- therefor.
In Column 29, Line 45, delete "hygiene" and insert -- hygiene products. -- therefor.

Signed and Sealed this
Twelfth Day of May, 2015

Michelle K. Lee
*Director of the United States Patent and Trademark Office*